US012233313B2

United States Patent
Chen et al.

(10) Patent No.: US 12,233,313 B2
(45) Date of Patent: Feb. 25, 2025

(54) CYCLING DETECTION METHOD, ELECTRONIC DEVICE AND COMPUTER-READABLE STORAGE MEDIUM

(71) Applicant: HONOR DEVICE CO., LTD., Shenzhen (CN)

(72) Inventors: Qing Chen, Shenzhen (CN); Xiaohan Chen, Shenzhen (CN); Teng Xu, Shenzhen (CN)

(73) Assignee: HONOR DEVICE CO., LTD., Shenzhen (CN)

( * ) Notice: Subject to any disclaimer, the term of this patent is extended or adjusted under 35 U.S.C. 154(b) by 299 days.

(21) Appl. No.: 17/923,882

(22) PCT Filed: Mar. 24, 2021

(86) PCT No.: PCT/CN2021/082617
§ 371 (c)(1),
(2) Date: Nov. 7, 2022

(87) PCT Pub. No.: WO2022/012079
PCT Pub. Date: Jan. 20, 2022

(65) Prior Publication Data
US 2023/0271059 A1      Aug. 31, 2023

(30) Foreign Application Priority Data
Jul. 14, 2020  (CN) .......................... 202010675334.4

(51) Int. Cl.
*A63B 24/00*    (2006.01)
*A63B 71/06*    (2006.01)

(52) U.S. Cl.
CPC ...... *A63B 24/0062* (2013.01); *A63B 71/0622* (2013.01); *A63B 2220/31* (2013.01); *A63B 2220/34* (2013.01); *A63B 2220/836* (2013.01)

(58) Field of Classification Search
CPC ............ A63B 24/0062; A63B 71/0622; A63B 2220/31; A63B 2220/34; A63B 2220/836;
(Continued)

(56) References Cited

U.S. PATENT DOCUMENTS 8,949,070 B1 * 2/2015 Kahn ................... G01C 22/006
                                                         702/158
9,936,912 B2    4/2018 Roovers et al.
(Continued)

FOREIGN PATENT DOCUMENTS

CN          105021208 A     11/2015
CN          105030260 A     11/2015
(Continued)

OTHER PUBLICATIONS

Wang Yongxiong et al., "Human action and road condition recognition based on the inertial information", Journal of Biomedical Engineering. 2018(04) p. 621-630.
(Continued)

*Primary Examiner* — Joshua Lee
(74) *Attorney, Agent, or Firm* — WOMBLE BOND DICKINSON (US) LLP

(57) ABSTRACT

A cycling detection method, an electronic device, and a computer-readable storage medium are provided. The cycling detection method includes: obtaining an acceleration signal and an angular velocity signal collected by a wearable device of a user's foot, and analyzing a time-domain feature of the acceleration signal, a frequency-domain feature of the acceleration signal, a time-domain feature of the angular velocity signal, and/or a frequency-domain feature of the angular velocity signal; filtering the acceleration signal and the angular velocity signal to obtain a target acceleration signal and a target angular velocity signal of the user's cycling if it is determined, based on an analysis result, that
(Continued)

a current status of the user is a cycling state; and determining a behavior feature of the user's cycling based on the target acceleration signal and the target angular velocity signal, where the behavior feature includes a cadence feature and a foot posture feature.

13 Claims, 15 Drawing Sheets

(58) Field of Classification Search
CPC .... A61B 5/1114; A61B 5/6829; G01D 21/02; G06F 2218/02; G06F 2218/08; G16H 20/30; G16H 40/60
See application file for complete search history.

(56) References Cited

U.S. PATENT DOCUMENTS

| | | | |
|---|---|---|---|
| 10,744,390 B1 * | 8/2020 | Kahn | G01C 22/006 |
| 10,881,906 B2 | 1/2021 | Nagasaka et al. | |
| 11,123,606 B2 * | 9/2021 | Nagasaka | A61B 5/1123 |
| 11,361,602 B2 | 6/2022 | Chen et al. | |
| 2015/0087995 A1 * | 3/2015 | Murai | A61B 5/684 |
| | | | 600/595 |
| 2015/0142370 A1 | 5/2015 | Leu | |
| 2015/0345952 A1 * | 12/2015 | Chang | G01C 21/12 |
| | | | 701/541 |
| 2016/0030807 A1 | 2/2016 | Matsumoto et al. | |
| 2016/0058372 A1 * | 3/2016 | Raghuram | A61B 5/681 |
| | | | 600/595 |
| 2017/0007166 A1 * | 1/2017 | Roovers | G01C 22/002 |
| 2017/0050080 A1 | 2/2017 | Mizuochi | |
| 2017/0138807 A1 | 5/2017 | Miau et al. | |
| 2017/0176187 A1 * | 6/2017 | Ishihama | G01C 21/08 |
| 2019/0038938 A1 * | 2/2019 | Nagasaka | A63B 24/0021 |
| 2019/0240541 A1 * | 8/2019 | Denton | A63B 22/025 |
| 2020/0107754 A1 | 4/2020 | Lin et al. | |
| 2020/0108884 A1 | 4/2020 | Przykucki, Jr. et al. | |
| 2020/0143237 A1 | 5/2020 | Gordon et al. | |

FOREIGN PATENT DOCUMENTS

| | | |
|---|---|---|
| CN | 105183158 A | 12/2015 |
| CN | 105311813 A | 2/2016 |
| CN | 105528613 A | 4/2016 |
| CN | 106030247 A | 10/2016 |
| CN | 106139563 A | 11/2016 |
| CN | 106161456 A | 11/2016 |
| CN | 106644208 A | 5/2017 |
| CN | 106933342 A | 7/2017 |
| CN | 107239147 A | 10/2017 |
| CN | 107948933 A | 4/2018 |
| CN | 108426577 A | 8/2018 |
| CN | 108634960 A | 10/2018 |
| CN | 108703760 A | 10/2018 |
| CN | 208065167 U | 11/2018 |
| CN | 109009142 A | 12/2018 |
| CN | 109276869 A | 1/2019 |
| CN | 109795592 A | 5/2019 |
| CN | 109886068 A | 6/2019 |
| CN | 110084286 A | 8/2019 |
| CN | 110245718 A | 9/2019 |
| CN | 110263870 A | 9/2019 |
| CN | 110411440 A | 11/2019 |
| CN | 111001144 A | 4/2020 |
| CN | 111044072 A | 4/2020 |
| CN | 210302323 U | 4/2020 |
| CN | 112504295 A | 3/2021 |
| EP | 3438607 A1 | 2/2019 |
| WO | 2019196106 A1 | 10/2019 |

OTHER PUBLICATIONS

Liu Shengzhong, "Research of Human Motion Pattern Recognition Method Based on MIMU", Southeast University, National 211 Project Universities National 985 Project Universities Universities directly under the Ministry of Education, May 2019, 76 pages.

Yang Yajun, "Design of Wearable Human Activity-Monitoring System Based on Accelerometer", Huazhong University of Science and Technology, Hubei Province National 211 Project Universities National 985 Project Universities Universities directly under the Ministry of Education, May 2019, 82 pages.

Stephen M. Cain, "Measurement of Bicycle and Rider Kinematics during Real-World Cycling Using a Wireless Array of Inertial Sensors", Proceedings, Bicycle and Motorcycle Dynamics 2016, Symposium on the Dynamics and Control of Single Track Vehicles, Sep. 21-23, 2016, Milwaukee, Wisconsin USA, 10 pages.

Hajime Kato et al., "Visualization Method for Bicycle Rider Behavior Analysis using a Smartphone", 2017 IEEE 41st Annual Computer Software and Applications Conference, Sep. 2017, p. 354-359.

Attila Reiss et al: "Activity Recognition Using Biomechanical Model Based Pose Estimation", Nov. 14, 2010 (Nov. 14, 2010), SAT 2015 18th International Conference, Austin, TX, USA, Sep. 24-27, 2015, 14 pages.

Yuting Zhang et al: "Monitoring walking and Cycling of Middle-Aged to Older Community Dwellers Using Wireless Wearable Accelerometers", Engineering in Medicine and Biology Society (EMBC), 2013 34th Annual International Conference of the IEEE, IEEE, Aug. 28, 2012 (Aug. 28, 2012), pp. 158-161.

* cited by examiner

CYCLING DETECTION METHOD, ELECTRONIC DEVICE AND COMPUTER-READABLE STORAGE MEDIUM

CROSS-REFERENCE TO RELATED APPLICATIONS

This application is a National Stage of International Application No. PCT/CN2021/082617, filed on Mar. 24, 2021, which claims priority to Chinese Patent Application No. 202010675334.4, filed on Jul. 14, 2020. Both of the aforementioned applications are hereby incorporated by reference in their entireties.

TECHNICAL FIELD

This application relates to the field of smart wearable devices, and in particular, to a cycling detection method, an electronic device, and a computer-readable storage medium.

BACKGROUND

In recent years, with the improvement of daily life, mass sports markets have seen an explosive development trend, and cycling has become a healthy and environmentally friendly leisure sport. Detecting cycling behavior of a user during cycling can guide the user's cycling. At present, a component for detecting the cycling behavior of the user is mainly a component installed on a bicycle. Because the component of the bicycle analyzes the cycling behavior of the user based on collected motion information of the bicycle, a relatively small amount of cycling behavior data of the user may be determined, and consequently a cycling behavior analysis result is not accurate enough. Moreover, installation of the component of the bicycle is complex, leading to poor user experience.

SUMMARY

This application provides a cycling detection method, an electronic device, and a computer-readable storage medium, which can collect a cadence and a foot motion angle of a user's cycling, to improve accuracy of a cycling behavior analysis result; and are easy for use, to improve user experience.

To achieve the foregoing objective, this application uses the following technical solutions.

According to a first aspect, a cycling detection method is provided, including: obtaining an acceleration signal and an angular velocity signal collected by a wearable device on a user's foot, and analyzing a time-domain feature of the acceleration signal, a frequency-domain feature of the acceleration signal, a time-domain feature of the angular velocity signal, and/or a frequency-domain feature of the angular velocity signal; filtering the acceleration signal and the angular velocity signal to obtain a target acceleration signal and a target angular velocity signal of the user's cycling if it is determined, based on an analysis result of the time-domain feature of the acceleration signal, the frequency-domain feature of the acceleration signal, the time-domain feature of the angular velocity signal, and/or the frequency-domain feature of the angular velocity signal, that a current status of the user is a cycling state; and determining a behavior feature of the user's cycling based on the target acceleration signal and the target angular velocity signal, where the behavior feature includes a cadence feature and a foot posture feature.

In an embodiment of this application, the acceleration signal and the angular velocity signal collected by the wearable device of the foot are obtained. First, a status of the user is identified based on the time-domain feature of the acceleration signal, the frequency-domain feature of the acceleration signal, the time-domain feature of the angular velocity signal, and the frequency-domain feature of the angular velocity signal. Then, the acceleration signal and the angular velocity signal are filtered to obtain the target acceleration signal and the target angular velocity signal of the user's cycling if the status of the user is the cycling state. An interference signal may be removed by determining the cycling state and performing filtering, to obtain accurate cycling data of the user, thereby improving calculation precision. Finally, a behavior feature of the user's cycling is determined based on a waveform feature of the target acceleration signal and a waveform feature of the target angular velocity signal of the user's cycling. The behavior feature of the user's cycling is determined based on the acceleration signal and the angular velocity signal of the user's foot collected during cycling. Therefore, when compared with determining the behavior feature of the user's cycling based on motion information of a bicycle, more behavior features of the user's cycling may be determined, including the cadence feature and the foot posture feature of the user's cycling, to improve accuracy of a cycling behavior analysis result and better guide the user's cycling. In addition, the wearable device on the foot is easy to use, thereby improving user experience with ease of use and practicability.

In a possible implementation of the first aspect, after the obtaining an acceleration signal and an angular velocity signal collected by a wearable device on a user's foot, the method further includes: determining a first road surface feature of the user's cycling based on the frequency-domain feature of the angular velocity signal. The first road surface feature is a road surface type, which is used to describe roughness of a road surface. For example, the first road surface feature may be a cement road surface, an asphalt road surface, a gravel road surface, or the like. Different road surfaces correspond to different angular velocity frequencies. The first road surface feature of the user's cycling may be determined based on a frequency in a frequency-domain signal of an angular velocity and a corresponding amplitude.

In a possible implementation of the first aspect, after the obtaining a target acceleration signal and a target angular velocity signal of the user's cycling, the method further includes: determining a second road surface feature of the user's cycling based on the target acceleration signal. The second road surface feature is a gradient of a road surface.

Specifically, the determining a second road surface feature based on the target acceleration signal includes:
  obtaining a prestored acceleration signal collected when the user is standing or walking; determining a direction of a gravity vector based on the acceleration signal collected when the user is standing or walking; determining a direction of a first acceleration vector of the user's cycling based on the acceleration signal collected when the user is standing or walking and the target acceleration signal, where the direction of the first acceleration vector is the same as a forward direction of the user's cycling; and determining the second road surface feature based on the direction of the first acceleration vector and the direction of the gravity vector.

In a possible implementation of the first aspect, after the determining the second road surface feature based on the direction of the first acceleration vector and the direction of the gravity vector, the method further includes:

constructing a three-dimensional coordinate system, where the three-dimensional coordinate system includes an X-axis, a Y-axis, and a Z-axis, the Y-axis represents an opposite direction of the gravity vector, the Z-axis represents a direction of an angular velocity, the direction of the angular velocity is determined by the target angular velocity signal, and the X-axis represents a horizontal direction; and determining, based on the first acceleration vector and the three-dimensional coordinate system, a cycling trajectory corresponding to the second road surface feature. Because the cycling trajectory is calculated in the three-dimensional coordinate system, the calculated cycling trajectory can reflect a spatial position change of the user. The cycling trajectory may include both a forward trajectory of the user's cycling on a road surface and a trajectory of left-right movement of the user's cycling on a road surface.

In a possible implementation of the first aspect, the method further includes: obtaining resistance and a cycling speed of the user's cycling; and calculating a cycling power of the user based on the resistance and the cycling speed, to guide the user's cycling.

In a possible implementation of the first aspect, the obtaining resistance of the user's cycling includes: obtaining a wind speed, a wind direction, and a weight of the user; and determining the resistance of the user's cycling based on the wind speed, the wind direction, and the weight of the user.

In a possible implementation of the first aspect, the method further includes: obtaining heart rate information of the user during cycling; and determining energy consumed by the user during cycling based on the heart rate information of the user during cycling and a preset calculation formula.

In a possible implementation of the first aspect, the method further includes: calculating, based on the cycling power, work done by the user during cycling; and calculating cycling efficiency of the user's cycling based on the work done by the user during cycling and the energy consumed by the user during cycling. A cycling status of the user may be determined based on the cycling efficiency, to guide the user's cycling.

In a possible implementation of the first aspect, the method further includes: obtaining preset cycling data; and generating a cycling guidance suggestion based on the preset cycling data, the cycling efficiency, the cycling power, the cadence feature, and the foot posture feature, to provide professional guidance for the user's cycling.

In a possible implementation of the first aspect, the method further includes: generating at least one of a corresponding text prompt, voice prompt, or vibration prompt based on the cycling guidance suggestion.

According to a second aspect, a cycling detection apparatus is provided, including:

a communication module, configured to obtain an acceleration signal and an angular velocity signal collected by a wearable device on a user's foot, and analyze a time-domain feature of the acceleration signal, a frequency-domain feature of the acceleration signal, a time-domain feature of the angular velocity signal, and/or a frequency-domain feature of the angular velocity signal;

a processing module, configured to filter the acceleration signal and the angular velocity signal to obtain a target acceleration signal and a target angular velocity signal of the user's cycling if it is determined, based on an analysis result of the time-domain feature of the acceleration signal, the frequency-domain feature of the acceleration signal, the time-domain feature of the angular velocity signal, and/or the frequency-domain feature of the angular velocity signal, that a current status of the user is a cycling state; and a storage module, configured to determine a behavior feature of the user's cycling based on the target acceleration signal and the target angular velocity signal, where the behavior feature includes a cadence feature and a foot posture feature.

In a possible implementation of the second aspect, the processing module is further configured to determine a first road surface feature of the user's cycling based on the frequency-domain feature of the angular velocity signal.

In a possible implementation of the second aspect, the processing module is further configured to determine a second road surface feature of the user's cycling based on the target acceleration signal.

In a possible implementation of the second aspect, the communication module is further configured to obtain a prestored acceleration signal collected when the user is standing or walking, and the processing module is further configured to determine a direction of a gravity vector based on the acceleration signal collected when the user is standing or walking; determining a direction of a first acceleration vector of the user's cycling based on the acceleration signal collected when the user is standing or walking and the target acceleration signal; and determining the second road surface feature based on the direction of the first acceleration vector and the direction of the gravity vector.

In a possible implementation of the second aspect, the processing module is further configured to:

construct a three-dimensional coordinate system, where the three-dimensional coordinate system includes an X-axis, a Y-axis, and a Z-axis, the Y-axis represents an opposite direction of the gravity vector, the Z-axis represents a direction of an angular velocity, the direction of the angular velocity is determined by the target angular velocity signal, and the X-axis represents a horizontal direction; and determine, based on the first acceleration vector and the three-dimensional coordinate system, a cycling trajectory corresponding to the second road surface feature.

In a possible implementation of the second aspect, the communication module is further configured to obtain resistance and a cycling speed of the user's cycling, and the processing module is further configured to calculate a cycling power of the user based on the resistance and the cycling speed.

In a possible implementation of the second aspect, the communication module is further configured to obtain a wind speed, a wind direction, and a weight of the user; and the processing module is further configured to determine the resistance of the user's cycling based on the wind speed, the wind direction, and the weight of the user.

In a possible implementation of the second aspect, the communication module is further configured to obtain heart rate information of the user during cycling; and the processing module is further configured to determine energy consumed by the user during cycling based on the heart rate information of the user during cycling and a preset calculation formula.

In a possible implementation of the second aspect, the processing module is further configured to calculate, based on the cycling power, work done by the user during cycling; and calculate cycling efficiency of the user's cycling based on the work done by the user during cycling and the energy consumed by the user during cycling.

In a possible implementation of the second aspect, the communication module is further configured to obtain preset cycling data; and
the processing module is further configured to generate a cycling guidance suggestion based on the preset cycling data, the cycling efficiency, the cycling power, the cadence feature, and the foot posture feature.

In a possible implementation of the second aspect, the processing module is further configured to generate at least one of a corresponding text prompt, voice prompt, or vibration prompt based on the cycling guidance suggestion.

According to a third aspect, an electronic device is provided, including a memory, a processor, and a computer program stored in the memory and executable on the processor. When the processor executes the computer program, the cycling detection method according to the foregoing first aspect is implemented.

According to a fourth aspect, a computer-readable storage medium is provided, where the computer-readable storage medium stores a computer program. When the computer program is executed by a processor, the cycling detection method according to the foregoing first aspect is implemented.

According to a fifth aspect, a computer program product is provided. When the computer program product is run on a terminal device, the terminal device is enabled to perform the cycling detection method according to the foregoing first aspect.

It can be understood that, for beneficial effects of the foregoing second aspect to fifth aspect, reference may be made to related descriptions in the foregoing first aspect. Details are not described herein again.

DESCRIPTION OF EMBODIMENTS

In the following description, for the purpose of illustration rather than limitation, specific details such as specific system structures and technologies are proposed, to help have a thorough understanding of embodiments of this application. However, a person skilled in the art shall understand that this application may be implemented in other embodiments without these specific details. In other cases, detailed descriptions about well-known systems, apparatuses, circuits, and methods are omitted, to prevent unnecessary details from obscuring descriptions of this application.

It should be understood that, when used in this specification of this application and the appended claims, the term "include" or "comprise" indicates the presence of the described characteristic, whole, step, operation, element, and/or component, but does not exclude presence or addition of one or more other characteristics, wholes, steps, operations, elements, components, and/or sets thereof.

It should be further understood that, the term "and/or" used in this specification of this application and the appended claims refers to and includes any combination or all possible combinations of one or more of the associated listed items.

As used in the specification of this application and the appended claims, the term if may be interpreted, depending on the context, as "when . . . " or "once" or "in response to determining" or "in response to detecting". Similarly, the phrases "if it is determined" or "if the [described condition or event] is detected" may be interpreted, depending on the context, as "once it is determined" or "in response to determining" or "once the [described condition or event] is detected" or "in response to detection of the [described condition or event]".

In addition, the terms "first", "second", and the like in the description of this application are merely used for the purpose of distinguishable description, and cannot be understood as indicating or implying relative importance.

Referring to "an embodiment" or "some embodiments" or the like described in this specification of this application means that a particular feature, structure, or characteristic described with reference to the embodiment is included in one or more embodiments of this application. Therefore, the phrases "in an embodiment," "in some embodiments," "in some other embodiments," "in another embodiment," and the like appearing in various places in this specification do not necessarily mean same embodiments, but mean "one or more but not all of embodiments" unless specifically emphasized otherwise. The terms "include", "comprise", "have"

and their variants mean "including but not limited to" unless specifically emphasized otherwise.

The following describes in detail embodiments of this application.

Figure 1:
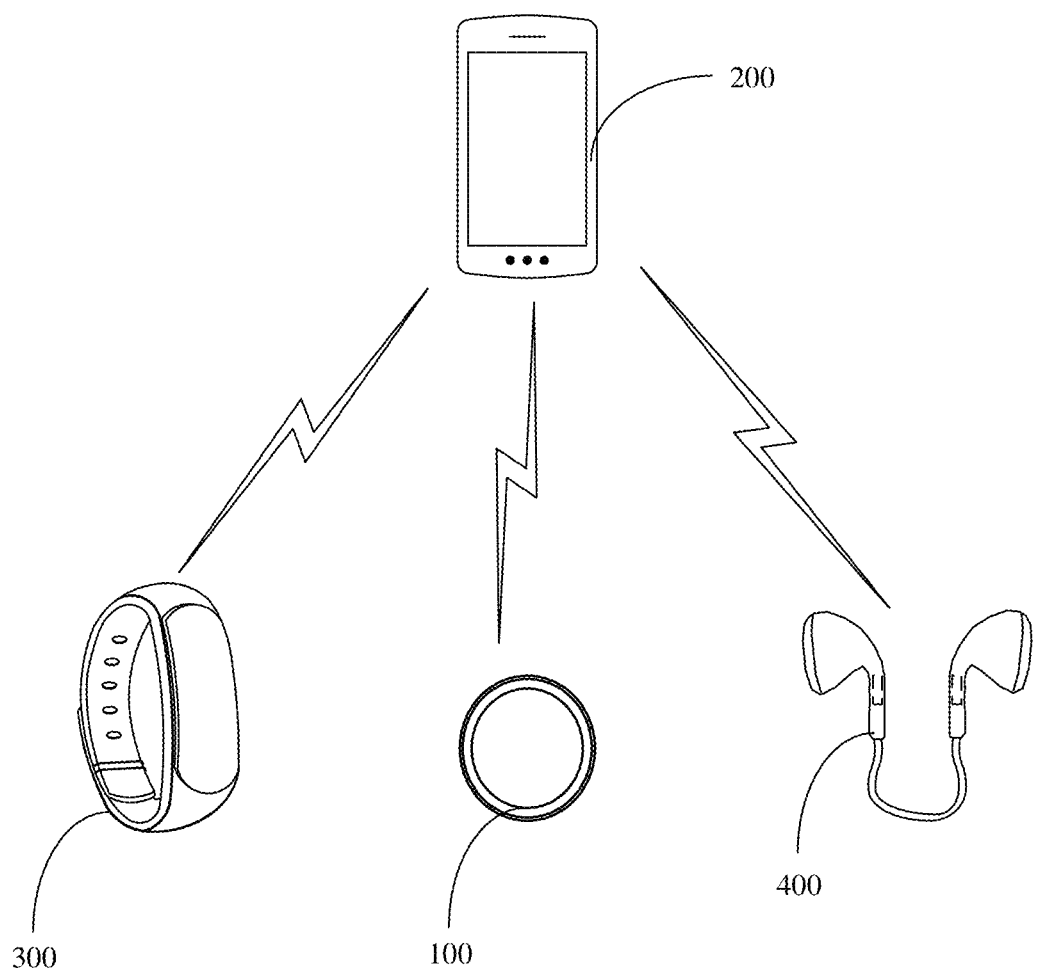
FIG. 1 is a schematic diagram of an architecture of a cycling detection system to which a cycling detection method is applicable according to an embodiment of this application.

As shown in FIG. 1, FIG. 1 shows an architecture of a cycling detection system to which a cycling detection method provided in an embodiment of this application is applicable. The system includes a first wearable device 100 and an electronic device 200. The first wearable device 100 is communicatively connected to the electronic device 200.

The first wearable device 100 is a wearable device that is worn on a user's foot, for example, a foot ring. The electronic device 200 may be a terminal device such as a mobile phone, a tablet computer, or a personal digital assistant (personal digital assistant, PDA).

Figure 2:
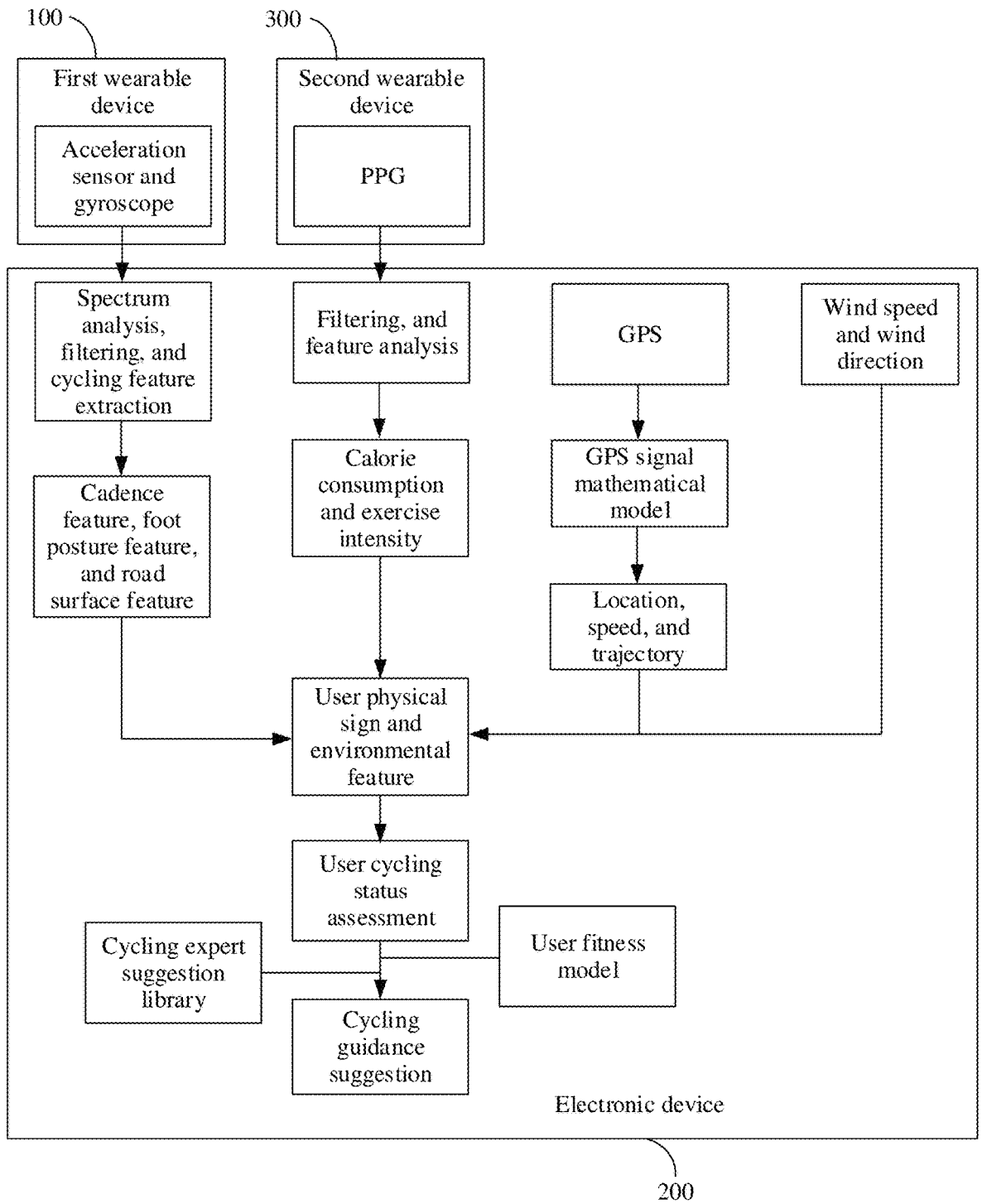
FIG. 2 is a schematic diagram of functions of devices in a cycling detection system according to an embodiment of this application.

As shown in FIG. 2, the first wearable device 100 may include an acceleration sensor and a gyroscope. The acceleration sensor is configured to collect an acceleration signal of the user's foot, and the gyroscope is configured to collect an angular velocity signal of the user's foot. The electronic device 200 obtains an acceleration signal and an angular velocity signal collected by a wearable device on a foot, and performs spectrum analysis on the acceleration signal and the angular velocity signal; filter the acceleration signal and the angular velocity signal and then extract cycling features of the filtered acceleration signal and angular velocity signal if it is obtained, based on spectrums of the acceleration signal and the angular velocity signal, that a current status of the user is a cycling state; and then obtain a cadence feature, a foot posture feature, and a road surface feature of the user's cycling based on the cycling features, so as to guide the user's cycling.

As shown in FIG. 1, in a possible implementation, the cycling detection system may further include a second wearable device 300. The second wearable device 300 is communicatively connected to the electronic device 200. The second wearable device 300 may be a wearable device that is worn on the user's wrist, for example, a wristband or a watch.

As shown in FIG. 2, the second wearable device 300 may include a photoplethysmography (photoplethysmograph, PPG) sensor, configured to collect physiological information of the user, where the physiological information of the user may include information such as a heart rate, blood oxygen, and a pulse. In this embodiment of this application, the electronic device 200 obtains heart rate information collected by the second wearable device 300, filters the heart rate information, performs feature analysis on the filtered heart rate information to obtain a heart rate and heart rate variability (Heart rate variability, HRV) of the user's cycling, and obtains energy consumed by the user during cycling, namely, calorie consumption, based on the heart rate and the HRV of the user's cycling. Exercise intensity of the user during cycling may be obtained based on the calorie consumption. For example, the electronic device 200 further includes a global positioning system (Global Positioning System, GPS), configured to collect location information of the user at each moment. The electronic device 200 obtains the location information, and obtains location information in a preset format, and a speed and a trajectory of movement of the user based on a GPS signal mathematical model and the location information stored in the electronic device 200. The electronic device 200 is further configured to obtain meteorological information, obtain a current wind speed and wind direction based on the meteorological information, and then calculate, based on a location, the speed, the trajectory, the wind speed, and the wind direction, work done by the user during cycling.

After calculating the cadence feature, the foot posture feature, the road surface feature, the calorie consumption, the exercise intensity, the location, the speed, and the trajectory of the user's cycling, and the work done during cycling, the electronic device 200 obtains, through statistical collection, a user physical sign and an environmental feature of the user, so that a cycling status of the user can be assessed. Preferably, after obtaining the cycling status of the user, the electronic device 200 may further obtain a physical fitness model of the user and preset cycling data stored in a cycling expert suggestion library. The physical fitness model of the user includes oxygen uptake, a body mass index (Body Mass Index, BMI), and the like. The cycling expert suggestion library is generated based on pre-collected cycling data of a large quantity of users and corresponding guidance suggestions. The preset cycling data is cycling data, corresponding to the physical sign or the environmental feature of the user, in the cycling expert suggestion library. The electronic device 200 obtains a cycling guidance suggestion based on the cycling state of the user, the physical fitness model, and the preset cycling data. The electronic device 200 then generates prompt information based on the cycling guidance suggestion, generates a corresponding text prompt based on the prompt information, and displays the text prompt in a display interface, or sends the text prompt to the second wearable device 300 so that the second wearable device 300 displays the text prompt in a display interface. The electronic device 200 may alternatively generate a corresponding vibration prompt based on the prompt information, and indicate the electronic device 200 or the second wearable device 300 to vibrate based on the vibration prompt, thereby guiding the user's cycling.

As shown in FIG. 1, in another possible implementation, the cycling detection system further includes an audio play device 400, and the audio play device 400 is communicatively connected to the electronic device 200. The audio play device 400 may be a headset or a speaker. After obtaining the cycling guidance suggestion, the electronic device 200 may generate a corresponding voice prompt based on the prompt information, and send the voice prompt to the audio play device 400. The audio play device 400 is configured to play a corresponding voice based on the voice prompt.

It should be noted that the function division of each device in the foregoing cycling detection system is merely used for description, and in actual application, the foregoing functions may be allocated to one or more devices for implementation as required. For example, the following functions of the electronic device 200 may be implemented by the first wearable device 100: obtaining an acceleration signal and an angular velocity signal collected by a wearable device on a foot, and performing spectrum analysis on the acceleration signal and the angular velocity signal; filtering the acceleration signal and the angular velocity signal and then extracting cycling features of the filtered acceleration signal and angular velocity signal if it is obtained, based on spectrums of the acceleration signal and the angular velocity signal, that a current status of the user is a cycling state; and then obtaining a cadence feature, a foot posture feature, and a road surface feature of the user's cycling based on the cycling features, so as to guide the user's cycling. The following functions of the electronic device 200 may be implemented by the second wearable device 300: obtaining collected heart rate information, filtering the heart rate information, performing feature analysis on the filtered heart rate information to obtain a heart rate and HRV of the user's cycling, and obtaining energy consumed by the user during cycling, namely, calorie consumption, based on the heart rate and the HRV of the user's cycling; and obtaining exercise intensity of the user during cycling based on the calorie consumption. Specific division of the functions is not limited in this application.

The following describes in detail a cycling detection method provided in an embodiment of this application based on the cycling detection system shown in FIG. 1 and FIG. 2 with reference to specific application scenarios.

Figure 3:
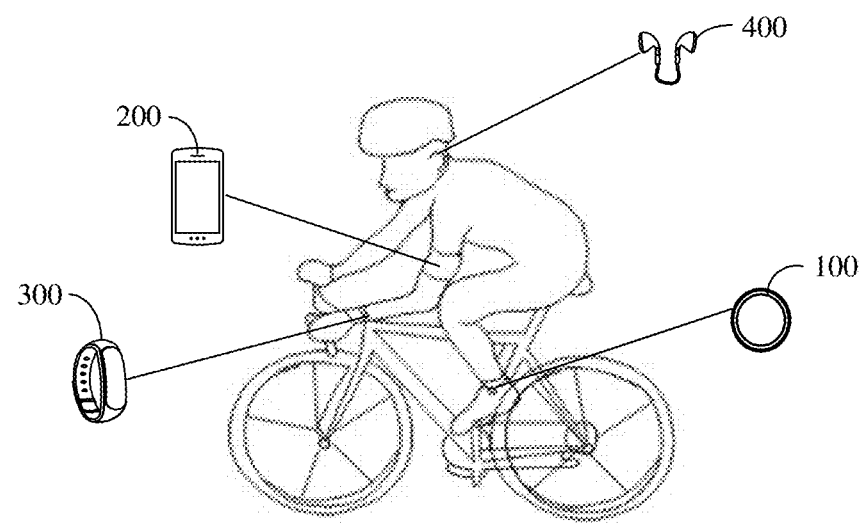
FIG. 3 is a diagram of an application scenario of a cycling detection method according to an embodiment of this application.

As shown in FIG. 3, in an application scenario, the electronic device 200 is a mobile phone, and the first wearable device 100 is communicatively connected to the electronic device 200. The first wearable device 100 collects an acceleration signal and an angular velocity signal, and sends the acceleration signal and the angular velocity signal to the electronic device 200. After receiving the acceleration signal and the angular velocity signal, the electronic device 200 analyzes a time-domain feature of the acceleration signal, a frequency-domain feature of the acceleration signal, a time-domain feature of the angular velocity signal, and the frequency-domain feature of the angular velocity signal, and determines, based on an analysis result, a time period corresponding to a cycling state.

Figure 4A:
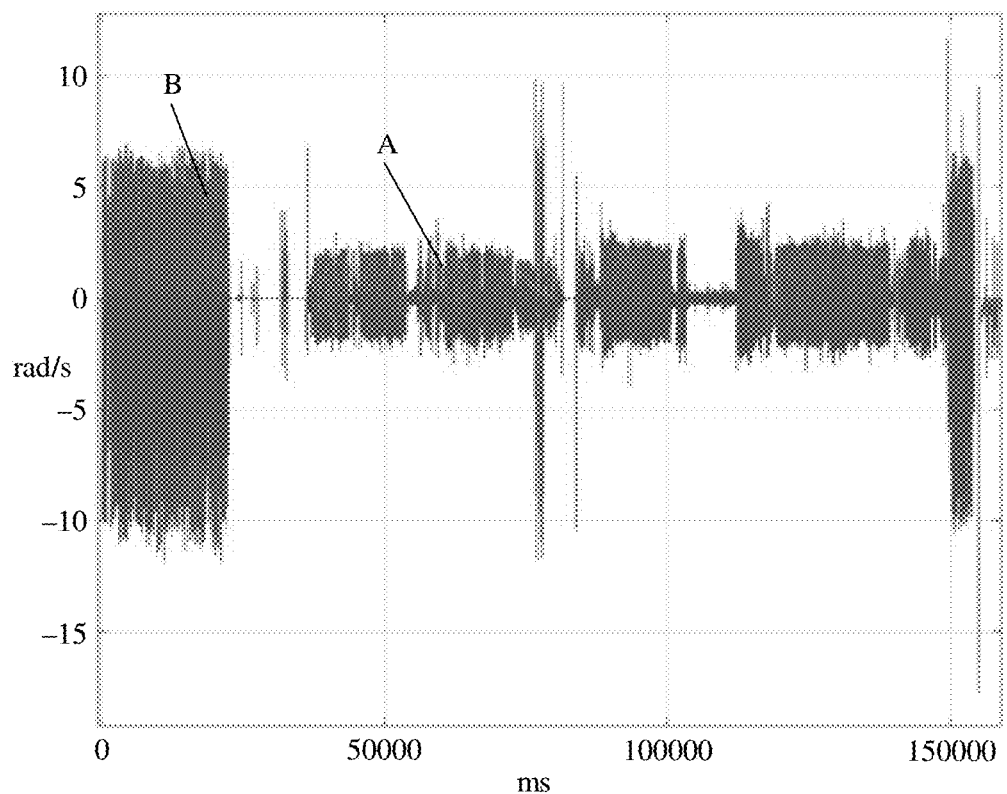
FIG. 4(a), FIG. 4(b), and FIG. 4(c) are schematic diagrams of a time-domain signal of an angular velocity according to an embodiment of this application.
Figure 4B:
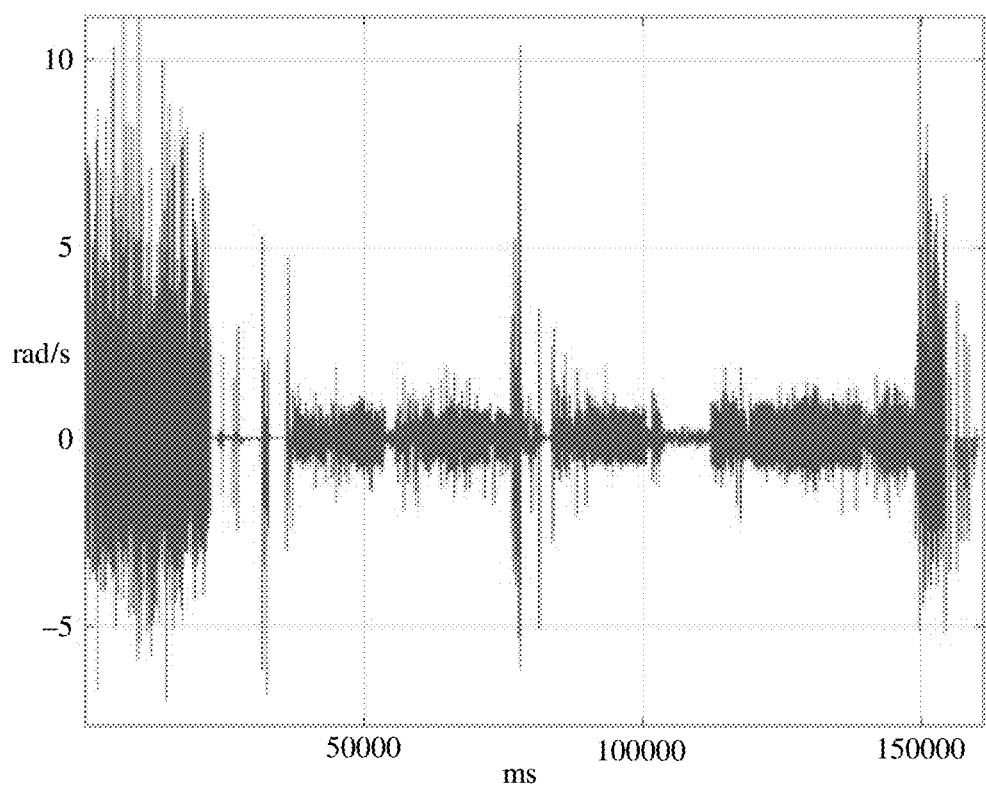
Figure 4C:
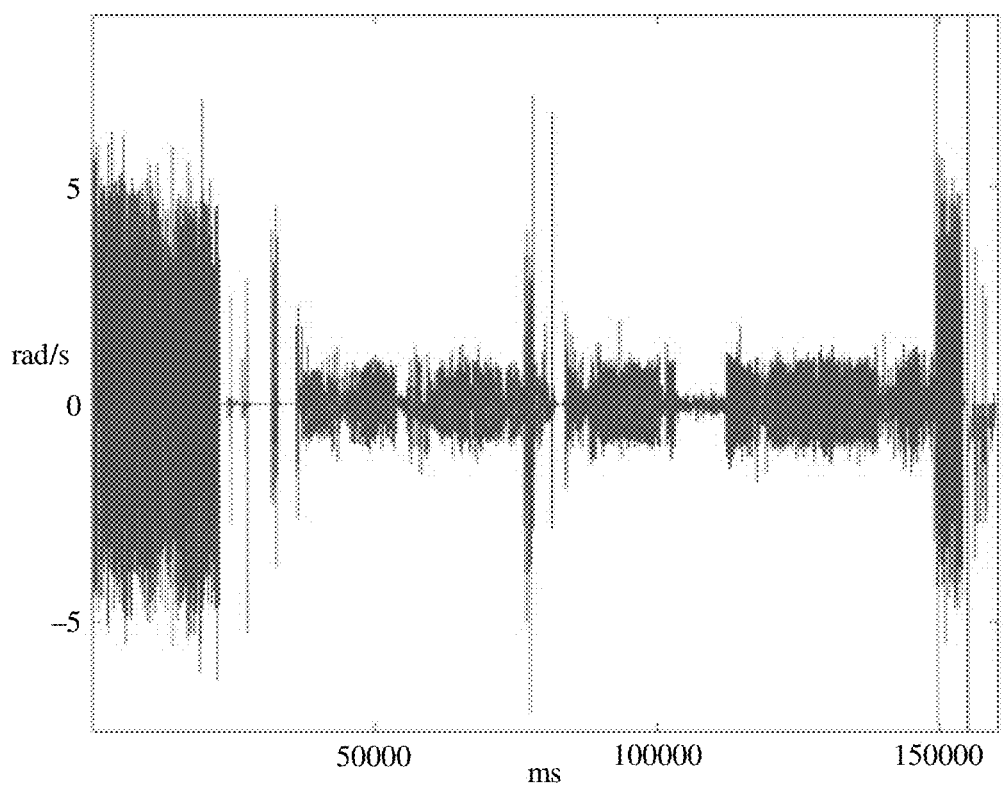

Specifically, the angular velocity signal collected by the first wearable device 100 is a time-domain signal of an angular velocity, and the acceleration signal collected by the first wearable device 100 is a time-domain signal of acceleration. As shown in FIG. 4(a), FIG. 4(b), and FIG. 4(c), FIG. 4(a) is a component of the time-domain signal of the angular velocity in an α direction, namely, a time-domain signal of the angular velocity in the α direction. FIG. 4(b) is a component of the time-domain signal of the angular velocity in a β direction, namely, a time-domain signal of the angular velocity in the β direction. FIG. 4(c) is a component of the time-domain signal of the angular velocity in a γ direction, namely, a time-domain signal of the angular velocity in the γ direction. In a coordinate system shown in FIG. 4(a), FIG. 4(b), and FIG. 4(c), an abscissa is measured in milliseconds (ms), and an ordinate is measured in radian per second (rad/s). The time-domain feature of the angular velocity signal includes an amplitude of the time-domain signal of the angular velocity in the α direction, an amplitude of the time-domain signal of the angular velocity in the β direction, and an amplitude of the time-domain signal of the angular velocity in the γ direction. The time-domain signals of the angular velocity in the three directions (the α direction, the β direction, and the γ direction) are converted into a frequency-domain signal, and filtering is performed based on a first preset frequency to obtain a frequency-domain signal of the angular velocity shown in FIG. 5. In a coordinate system shown in FIG. 5, an abscissa is measured in frequency (Hz), and an ordinate represents a signal quantity corresponding to the frequency. The frequency-domain feature of the angular velocity signal is an amplitude of the frequency-domain signal of the angular velocity. The first preset frequency is set based on experience values of angular velocity frequencies during movement of the user, for example, may be 0 to 5 Hz. The filtering performed based on the preset frequency can remove an interference signal caused by a road surface factor and improve data analysis efficiency.

Similarly, a time-domain signal of the acceleration in the α direction, a time-domain signal of the acceleration in the β direction, and a time-domain signal of the acceleration in the γ direction are converted into a frequency-domain signal, and filtering is performed based on a second preset frequency to obtain a frequency-domain signal of the acceleration. The second preset frequency is set based on experience values of acceleration frequencies during movement of the user. The time-domain feature of the acceleration signal includes an amplitude of the time-domain signal of the acceleration in the α direction, an amplitude of the time-domain signal of the acceleration in the β direction, and an amplitude of the time-domain signal of the acceleration in the γ direction. The frequency-domain feature of the acceleration signal is an amplitude of the frequency-domain signal of the acceleration.

The electronic device 200 analyzes a status of the user in each time period based on the amplitudes of the time-domain signal of the angular velocity in the three directions, the amplitude of the frequency-domain signal of the angular velocity, the amplitudes of the time-domain signal of the acceleration in the three directions, and the amplitude of the frequency-domain signal of the acceleration. The status of the user includes a cycling state, a stationary state, a walking state, and a running state. If the amplitudes of the time-domain signal of the angular velocity in the three directions, the amplitude of the frequency-domain signal of the angular velocity, the amplitudes of the time-domain signal of the acceleration in the three directions, and the amplitude of the frequency-domain signal of the acceleration are all within preset amplitude ranges in a specific time period, this time period is considered as a time period corresponding to the cycling state. That is, in this time period, the status of the user is the cycling state.

For example, it is assumed that preset amplitude ranges of the angular velocity signal corresponding to the cycling state are as follows: the amplitude of the time-domain signal of the angular velocity in the α direction ranges from 1 to 3, the amplitude of the time-domain signal of the angular velocity in the β direction ranges from 0.5 to 2, and the amplitude of the time-domain signal of the angular velocity in the γ direction ranges from 0.5 to 2. In addition, there is a band with an amplitude greater than 0.1 in a range of 0 to 1 Hz of the frequency-domain signal of the angular velocity. As shown in FIG. 4(a), FIG. 4(b), and FIG. 4(c), in a time period A in FIG. 4(a), FIG. 4(b), and FIG. 4(c), the amplitude of the time-domain signal of the angular velocity in the α direction ranges from 1 to 3, the amplitude of the time-domain signal of the angular velocity in the β direction ranges from 0.5 to 2, and the amplitude of the time-domain signal of the angular velocity in the γ direction ranges from 0.5 to 2. In addition, there is a band with an amplitude greater than 0.1 in a range of 0 to 1 Hz in FIG. 5. In this case, the amplitudes of the time-domain signal of the angular velocity in the three directions and the amplitude of the frequency-domain signal of the angular velocity are within preset amplitude ranges. Similarly, the amplitudes of the time-domain signal of the acceleration in the three directions and the amplitude of the frequency-domain signal of the acceleration are analyzed, and if the amplitudes of the time-domain signal of the acceleration in the three directions and the amplitude of the frequency-domain signal of the acceleration are all within preset amplitude ranges, the time period A is a time period corresponding to the cycling state. Similarly, a time period corresponding to the walking state may be determined based on preset amplitude ranges of the angular velocity signal corresponding to the specified walking state. For example, a time period B in FIG. 4(a), FIG. 4(b), and FIG. 4(c) is a time period corresponding to the walking state.

It should be noted that, in other feasible implementations, whether the current status of the user is the cycling state may be determined based on any one or more analysis results of the time-domain feature of the acceleration signal, the frequency-domain feature of the acceleration signal, the time-domain feature of the angular velocity signal, and the frequency-domain feature of the angular velocity signal. For example, if any one of the amplitudes of the time-domain signal of the angular velocity in the three directions, the amplitude of the frequency-domain signal of the angular velocity, the amplitudes of the time-domain signal of the angular velocity in the three directions, and the amplitude of the frequency-domain signal of the angular velocity is within the preset amplitude range, a corresponding time period is considered as a time period corresponding to the cycling state, and an acceleration signal and an angular velocity signal corresponding to this time period are an acceleration signal and an angular velocity signal corresponding to the cycling state. For example, if the amplitudes of the time-domain signals of the angular velocities in the three directions are all within the preset amplitude ranges in a specific time period, this time period is considered as a time period corresponding to the cycling state. For another example, if there is a band with an amplitude greater than 0.1 in a range of 0.2 to 0.7 Hz of the frequency-domain signal of the angular velocity, a frequency-domain signal in the range of 0.2 to 0.7 Hz is converted into a time-domain signal to obtain a time period corresponding to the cycling state.

Figure 5:
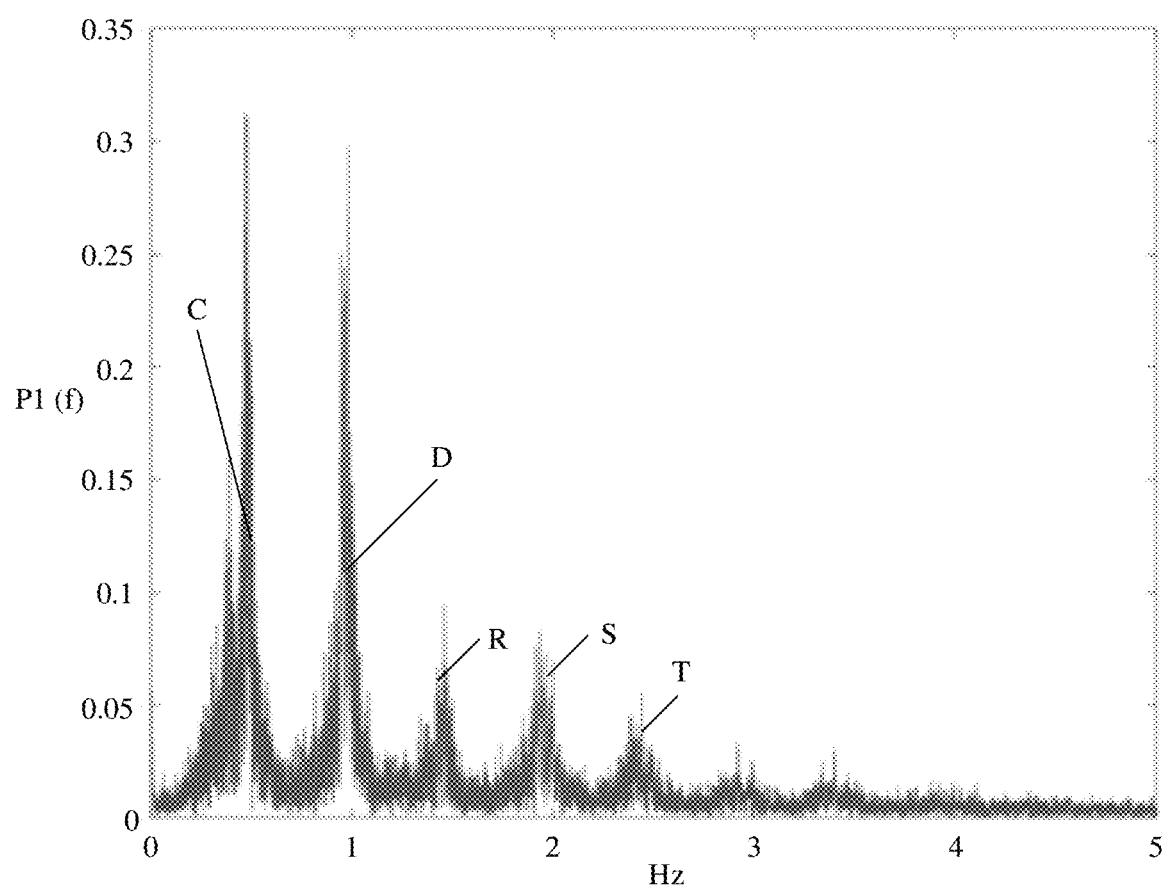
FIG. 5 is a schematic diagram of a frequency-domain signal of an angular velocity according to an embodiment of this application.

After determining the time period corresponding to the cycling state, the electronic device 200 obtains a third preset frequency. The third preset frequency is set based on experience values of angular velocity frequencies of the cycling state, for example, the third preset frequency ranges from 0.2 to 0.7 Hz. The electronic device 200 determines a largest amplitude in the third preset frequency range from the frequency-domain signal of the angular velocity, and then determines, based on a frequency corresponding to the largest amplitude in the third preset frequency range, an angular velocity frequency corresponding to the cycling state. For example, it is assumed that the third preset frequency ranges from 0.2 to 0.7 Hz, as shown in FIG. 5, if a largest amplitude in the range of 0.2 to 0.7 Hz is 0.31, and a frequency corresponding to the largest amplitude is 0.4 Hz, 0.4±0.1 Hz is used as the angular velocity frequency corresponding to the cycling state. That is, an angular velocity frequency band corresponding to the cycling state is 0.3 to 0.5 Hz, namely, a frequency band C in FIG. 5. Similarly, an acceleration frequency corresponding to the cycling state is determined from the frequency-domain signal of the acceleration based on a fourth preset frequency. If the status of the user includes the walking state, according to a similar method, an angular velocity frequency corresponding to the walking state may be determined from the frequency-domain signal of the angular velocity, and an acceleration frequency corresponding to the walking state may be determined from the frequency-domain signal of the acceleration. For example, a frequency band D in FIG. 5 is the angular velocity frequency corresponding to the walking state.

After determining the angular velocity frequency corresponding to the cycling state and the acceleration frequency corresponding to the cycling state, the electronic device 200 filters the angular velocity signal based on the angular velocity frequency corresponding to the cycling state to obtain a target angular velocity signal of the user's cycling, and filters the acceleration signal based on the acceleration frequency corresponding to the cycling state to obtain a target acceleration signal of the user's cycling. The electronic device 200 may determine a behavior feature of the user's cycling based on the target acceleration signal and the target angular velocity signal. The behavior feature includes a cadence feature, a foot posture feature, a gliding time period during cycling, whether a seat height is appropriate, and the like. Guidance can be provided for the user's cycling based on the behavior feature of the user's cycling.

Figure 6A:
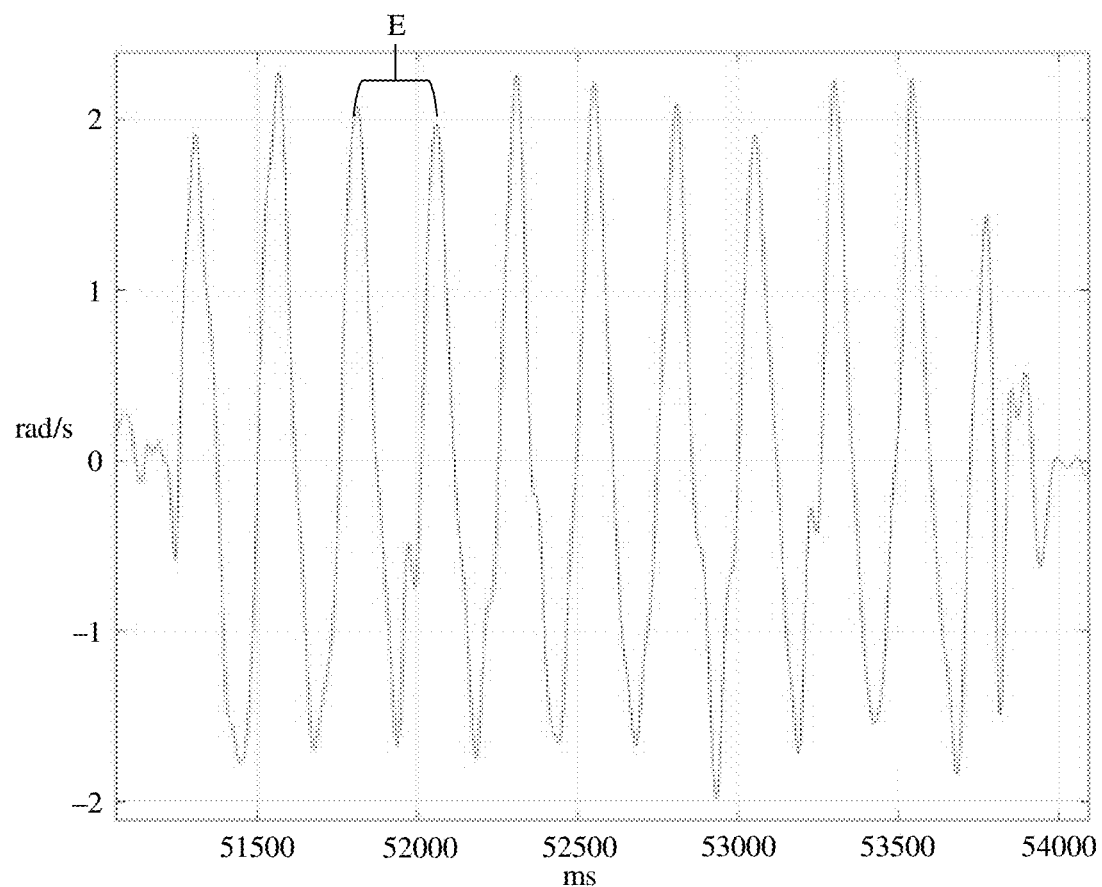
FIG. 6(a), FIG. 6(b), and FIG. 6(c) are schematic diagrams of a target angular velocity according to an embodiment of this application.
Figure 6B:
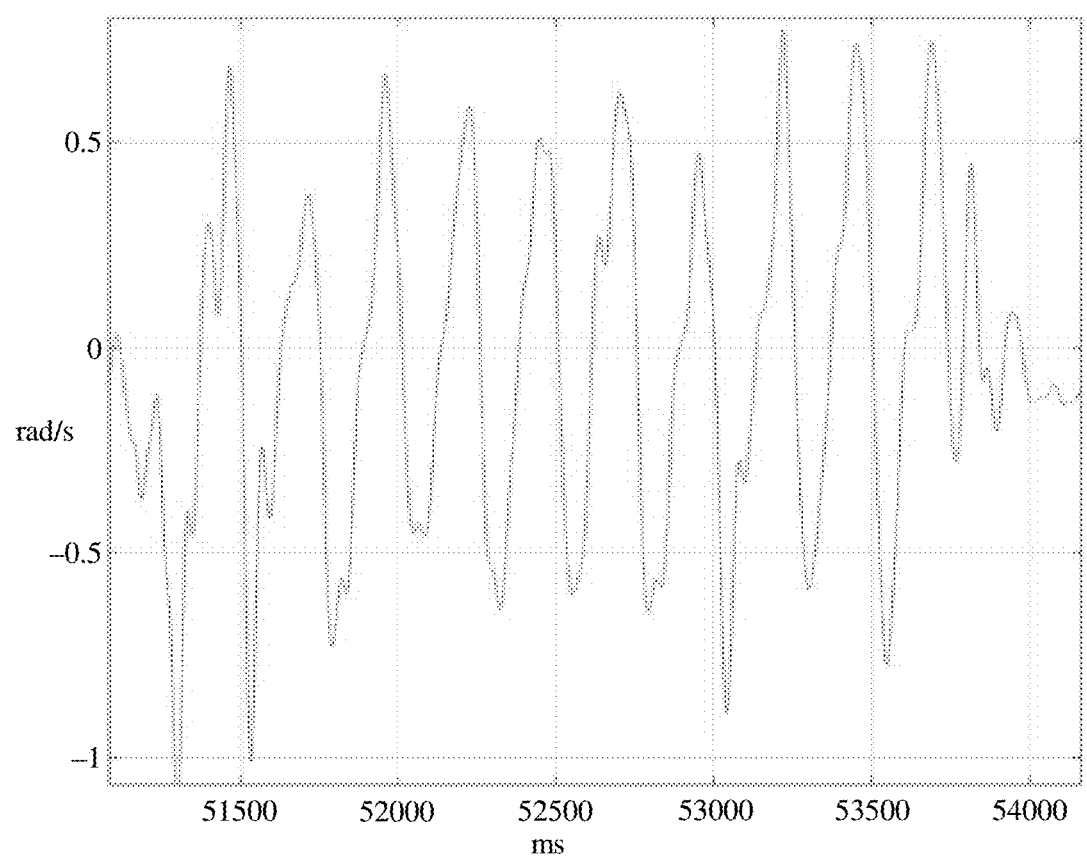
Figure 6C:
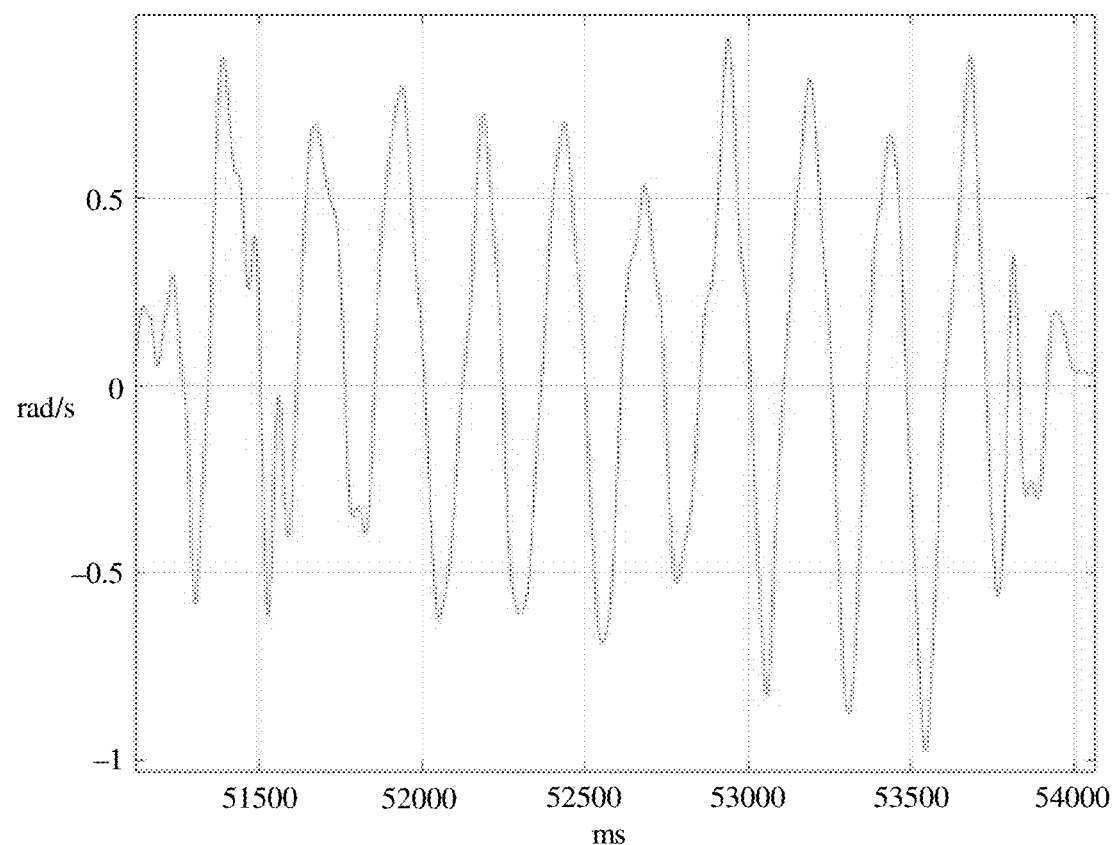

Specifically, as shown in FIG. 6(a), FIG. 6(b), and FIG. 6(c), FIG. 6(a) is a component of the target angular velocity signal in the α direction, FIG. 6(b) is a component of the target angular velocity signal in the β direction, and FIG. 6(c) is a component of the target angular velocity signal in the γ direction. In a coordinate system shown in FIG. 6(a), FIG. 6(b), and FIG. 6(c), an abscissa is measured in milliseconds (ms), and an ordinate is measured in radian per second (rad/s). Periods of the target angular velocity signal in the three directions are the same, and the period of the target angular velocity signal is a period of pedaling during the user's cycling. For example, duration corresponding to a time period E in FIG. 6(a), FIG. 6(b), and FIG. 6(c) is one of the periods of pedaling, a frequency at which the user pedals during cycling, namely, a cadence, may be calculated based on the period of pedaling. In each half period, the component of the target angular velocity signal in the α direction, the component of the target angular velocity signal in the β direction, and the component of the target angular velocity signal in the γ direction are integrated to obtain a change of the angular velocity in the half period. The change of the angular velocity in the half period is a foot motion angle during the user's cycling. A foot motion angle in each time period of the user's cycling, namely, the foot posture feature of the user's cycling, may be obtained based on a foot motion angle of each period, to guide the user's cycling.

Figure 7:
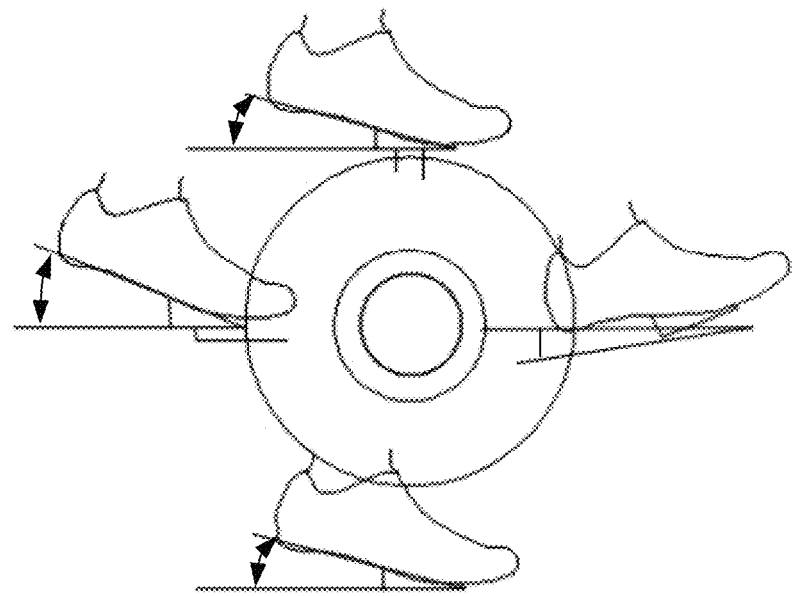
FIG. 7 is a schematic diagram of a foot position at each moment of a user's cycling according to an embodiment of this application.

In a possible implementation, as shown in FIG. 7, the electronic device 200 may determine a pedal position at each moment of the user's cycling based on the target angular velocity signal and a preset correspondence between a target angular velocity and a pedal position, and then may calculate a foot position at each moment of the user's cycling based on the foot motion angle at each moment of the user's cycling. A foot placement status at each moment of the user's cycling may be calculated based on the foot position and the pedal position at each moment of the user's cycling. The foot placement status at each moment of the user's cycling is compared with a preset placement status. If the foot placement status at each moment matches the preset placement status, it indicates that the seat height of the user during cycling is appropriate; otherwise, it indicates that the seat height of the user during cycling is not appropriate. The electronic device 200 further obtains, from the target angular velocity signal, a time period in which an angular velocity value is 0. This time period is a gliding time period of the user's cycling, namely, a time period in which the user's foot is placed on the pedal and does not pedal during cycling.

In another application scenario, the electronic device 200 is a mobile phone, and the first wearable device 100 is communicatively connected to the electronic device 200. The first wearable device 100 collects an acceleration signal and an angular velocity signal, and sends the acceleration signal and the angular velocity signal to the electronic device 200, that is, sends a time-domain signal of acceleration and a time-domain signal of an angular velocity to the electronic device 200. After receiving the time-domain signal of the angular velocity, the electronic device 200 obtains a frequency-domain signal of the angular velocity based on the time-domain signal of the angular velocity, and obtains a first road surface feature of the user's cycling based on an amplitude of the frequency-domain signal of the angular velocity, namely, a frequency-domain feature of the angular velocity signal. After obtaining the time-domain signal of the acceleration, the electronic device 200 filters the time-domain signal of the acceleration to obtain a target acceleration signal, and determines a second road surface feature of the user's cycling based on the target acceleration signal. The first road surface feature reflects smoothness of a road surface, and the second road surface feature is a gradient of the road surface.

Specifically, the first road surface feature may include a cement road surface, an asphalt road surface, a gravel road surface, tactile paving, and the like. Each road surface corresponds to a frequency range. The electronic device 200 detects whether there is a band with an amplitude greater than a preset value in each frequency range of the frequency-domain signal of the angular velocity. If there is a band with an amplitude greater than the preset value, it indicates that the first road surface feature includes a road surface corresponding to the frequency range.

For example, the cement road surface corresponds to a first frequency, the asphalt road surface corresponds to a second frequency, the gravel road surface corresponds to a third frequency, and the tactile paving corresponds to a fourth frequency. The electronic device 200 sequentially detects, in the frequency-domain signal of the angular velocity, whether there is a band with an amplitude greater than the preset value in the first frequency range, the second frequency range, the third frequency range, and the fourth frequency range, and determines the first road surface feature based on the determined frequency range in which the amplitude greater than the preset value is located. For example, if in the frequency-domain signal of the angular velocity, there is a band with an amplitude greater than the preset value in the first frequency range, it indicates that the first road surface feature includes the cement road surface. If in the frequency-domain signal of the angular velocity, there is a band with an amplitude greater than the preset value in the second frequency range, it indicates that the first road surface feature includes the asphalt road surface. Similarly, whether the first road surface feature includes the gravel road surface or the tactile paving may be obtained. For example, in FIG. 5, a frequency range R, a frequency range S, and a frequency range T each correspond to a road surface, and there are bands with amplitudes greater than preset values in the frequency range R, the frequency range S, and the frequency range T. In this case, the first road surface feature includes three types of road surfaces.

Figure 8:
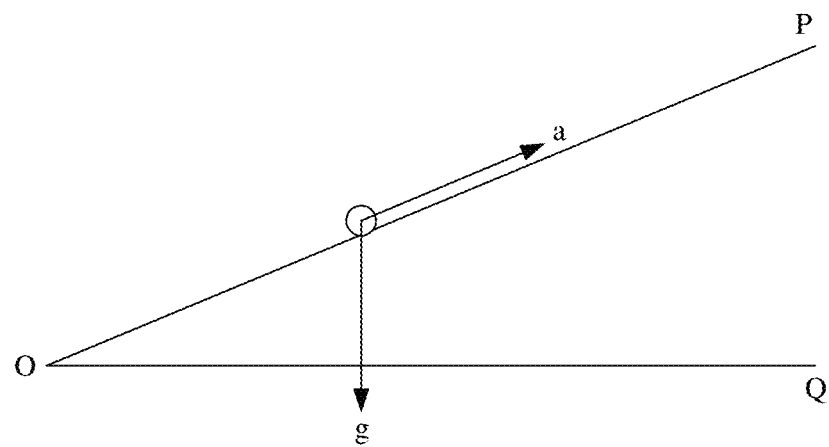
FIG. 8 is a schematic diagram of calculating a gradient of a road surface according to an embodiment of this application.

A process of calculating a gradient of a road surface is as follows: the electronic device first obtains an acceleration signal collected by the wearable device on the user's foot when the user is standing or walking, where the acceleration signal collected when the user is standing or walking may be prestored in the electronic device 200; or may determine, from the obtained acceleration signal, a time period in which the user is in a standing statue or a walking state, and then determine, based on the time period in which the user is in the standing state or the walking state, the acceleration signal collected when the user is standing or walking. The acceleration signal collected when the user is standing or walking is an acceleration signal in a direction of gravity. Because the target acceleration signal is an acceleration signal detected by an acceleration sensor during user's cycling, it represents a resultant acceleration signal during the user's cycling. If the user is cycling on a slope road, an acceleration signal in the direction of gravity is removed from a target acceleration signal of at least one period to obtain a first acceleration signal. The first acceleration signal is an acceleration signal used for moving forward along the road surface during the user's cycling. A preset principal component analysis method is used to perform principal component analysis on the first acceleration signal, to obtain a first acceleration vector. A direction of the first acceleration vector is the same as a forward direction of the user's cycling, that is, parallel to the road surface. Then, the gradient of the road surface may be determined based on the direction of the first acceleration vector and a direction of a gravity vector, where the direction of the gravity vector is the direction of gravity. For example, as shown in FIG. 8, g is the gravity vector, a is the first acceleration vector, and ∠POQ is the gradient of the road surface. An included angle between the gravity vector and the first acceleration vector may be calculated based on the direction of the gravity vector and the direction of the first acceleration vector. The included angle between the gravity vector and the first acceleration vector minus 90° is the gradient of the road surface.

Figure 9:
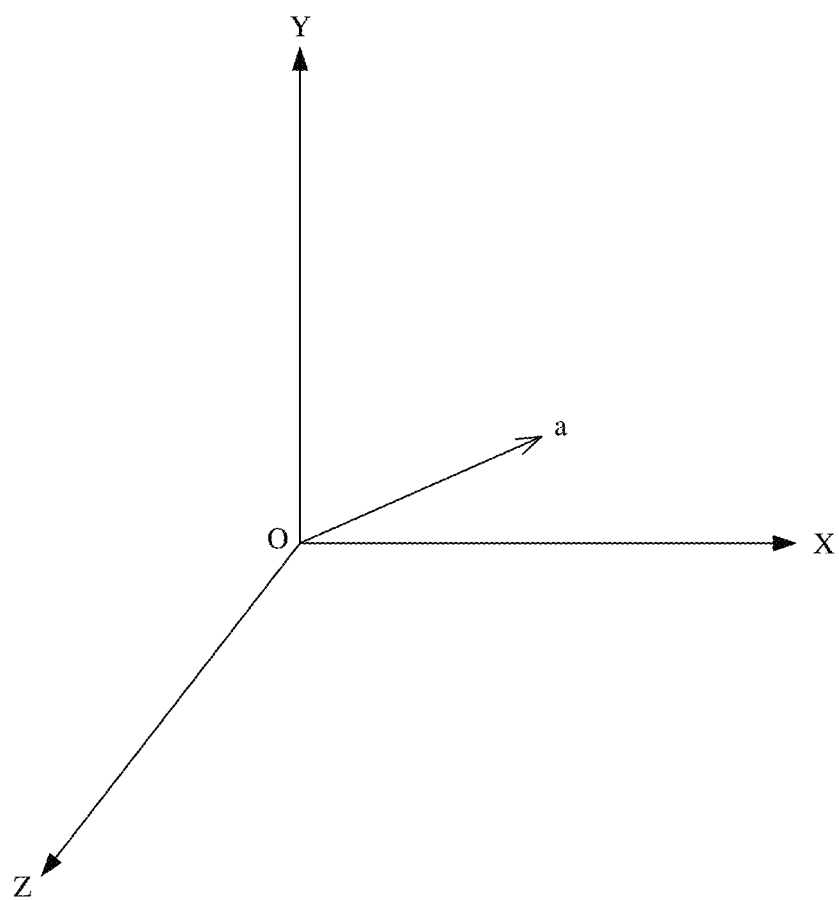
FIG. 9 is a schematic diagram of a first acceleration vector in a three-dimensional coordinate system according to an embodiment of this application.

Preferably, after the direction of the gravity vector is determined, principal component analysis is performed on a target angular velocity signal of at least one period to obtain a lateral cycling vector. A direction of the lateral cycling vector is a direction of the angular velocity, and the direction of the angular velocity is perpendicular to a plane on which a bicycle is located. A three-dimensional coordinate system may be constructed based on the direction of the gravity vector and the direction of the angular velocity. Then, a moving trajectory in the three-dimensional coordinate system during the user's cycling, namely, a cycling trajectory of the user on a slope road surface, may be calculated based on the first acceleration vector and a preset trajectory calculation formula corresponding to the three-dimensional coordinate system. Specifically, as shown in FIG. 9, an opposite direction of the gravity vector is used as a Y-axis, the direction of the angular velocity is used as a Z-axis, an X-axis is determined based on the Y-axis and Z-axis, and in this case, the X-axis is along a horizontal direction. After the three-dimensional coordinate system is constructed, the first acceleration vector a is decomposed in the three-dimensional coordinate system based on a value and the direction of the first acceleration vector a. For example, the first acceleration vector is decomposed into components in the three directions: the X-axis, the Y-axis, and the Z-axis. That is, the first acceleration vector is decomposed into three acceleration components. After the three acceleration components are obtained, a corresponding displacement component in the X-axis, a corresponding displacement component in the Y-axis, and a corresponding displacement component in the Z-axis are obtained based on the three acceleration components and a preset displacement calculation formula. Coordinates in the three-dimensional coordinate system during the user's cycling may be calculated based on the displacement components in the three directions. According to a similar method, coordinates in the three-dimensional coordinate system at each moment of the user's cycling are calculated. A moving trajectory in the three-dimensional coordinate system during the user's cycling, namely, a cycling trajectory of the user on a slope road surface, may be obtained based on the coordinates in the three-dimensional coordinate system at each moment. The cycling trajectory includes both a forward trajectory on the road surface during the user's cycling and a left-right moving trajectory on the road surface during the user's cycling.

In a possible implementation, after calculating a foot motion angle based on the target angular velocity signal, the electronic device 200 determines a moment at which the foot motion angle reaches a largest value in each period of the target angular velocity signal, and then obtains an angular velocity when the foot motion angle reaches the largest value. If the angular velocity at this moment is not 0, the angular velocity at this moment is corrected to 0, and a correction coefficient is determined. After the correction coefficient is determined, a corrected target angular velocity signal is determined based on the correction coefficient and the target angular velocity signal, and the direction of the angular velocity is re-determined based on the corrected target angular velocity signal, that is, the direction of the Z-axis is corrected. A three-dimensional coordinate system is constructed based on the re-determined direction of the Z-axis to obtain a corrected three-dimensional coordinate system, and then the cycling trajectory of the user is calculated based on the corrected three-dimensional coordinate system, to obtain a more accurate cycling trajectory.

Figure 10:
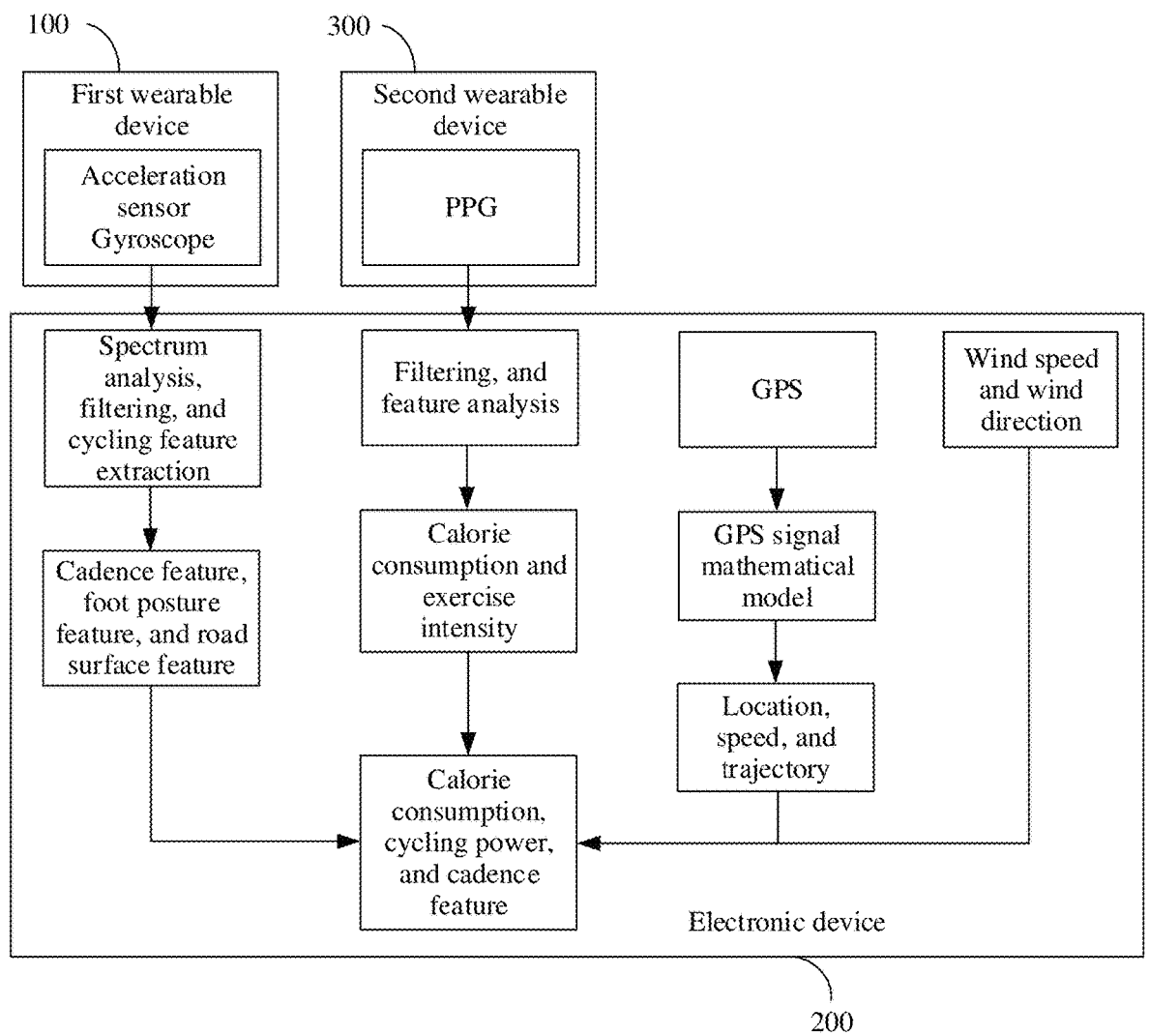
FIG. 10 is a schematic diagram of a method for determining a cycling state according to an embodiment of this application.

As shown in FIG. 10, in still another application scenario, the electronic device 200 is a mobile phone, and both the first wearable device 100 and the second wearable device 300 are communicatively connected to the electronic device 200. An acceleration sensor of the first wearable device 100 collects an acceleration signal of the user's foot, and a gyroscope collects an angular velocity signal of the user's foot. After receiving the acceleration signal and the angular velocity signal, the electronic device 200 performs spectrum analysis on the acceleration signal and the angular velocity signal; and filter the acceleration signal and the angular velocity signal and then extract cycling features of the filtered acceleration signal and angular velocity signal to obtain a target acceleration signal and a target angular velocity signal of the user's cycling if it is obtained, based on spectrums of the acceleration signal and the angular velocity signal, that a current status of the user is a cycling state. Then, a cadence feature, a foot posture feature, and a road surface feature of the user's cycling are obtained based on the target acceleration signal and the target angular velocity signal, where the road surface feature includes a first road surface feature and a second road surface feature.

A PPG sensor of the second wearable device 300 collects heart rate information of the user. After receiving the heart rate information of the user, the electronic device 200 filters the heart rate information of the user, then obtains a heart rate of the user during cycling from the filtered heart rate information with reference to a time period of the user's cycling, and then performs feature analysis on the heart rate of the user during cycling to obtain HRV. For example, the HRV is obtained by analyzing a time-domain feature and a frequency-domain feature of the heart rate of the user during cycling. Energy consumed by the user during cycling is calculated based on a preset energy calculation formula, the heart rate of the user during cycling, and the HRV. For example, oxygen consumption of the user during cycling may be obtained based on the heart rate of the user during cycling and the HRV, energy consumed by the user during cycling may be calculated based on the oxygen consumption, that is, calorie consumption of the user during cycling may be calculated.

The electronic device 200 further includes a GPS, and the GPS collects location information of the user during cycling. The electronic device 200 obtains location information in a preset format, and a cycling speed and trajectory of the user based on a GPS signal mathematical model and the location information stored in the electronic device 200. For example, the electronic device 200 converts obtained latitude and longitude data into coordinates in a coordinate system, and may calculate the speed and the trajectory of the user's cycling based on coordinates at each moment.

The electronic device 200 may further obtain weather information, for example, obtain weather information from a weather application program, obtain a wind speed and a wind direction based on the weather information, and obtain a wind speed and a wind direction during the user's cycling based on a cycling time period of the user. The electronic device 200 determines wind resistance during cycling based on the wind speed, the wind direction, and the cycling speed, and obtains, based on the speed and the wind resistance of the user's cycling, a power of work done by the user to overcome the wind resistance during cycling. The electronic device 200 further obtains a weight of the user pre-entered by the user, and obtains, based on a gradient of a road surface during the user's cycling, a speed, and the weight of the user, a power of work done by the user to overcome the gravity during cycling. The electronic device 200 further obtains preset friction force experience values, and obtains, based on the preset friction force experience values and the speed of the user's cycling, a power of work done by user to overcome the friction force during cycling. The electronic device 200 performs a sum operation on the power of work done by the user to overcome the frictional force during cycling, the power of work done to overcome the gravity, and the power of work done to overcome the wind resistance, to obtain a power of work done by the user to overcome the resistance during the user's cycling, namely, a cycling power. The electronic device 200 outputs a cadence, the calorie consumption, and the cycling power of the user's cycling based on a calculation result. The cadence, the calorie consumption, and the cycling power of the user's cycling are the cycling status of the user. The user can assess the cycling status based on an output result, to guide the user's cycling.

Figure 11:
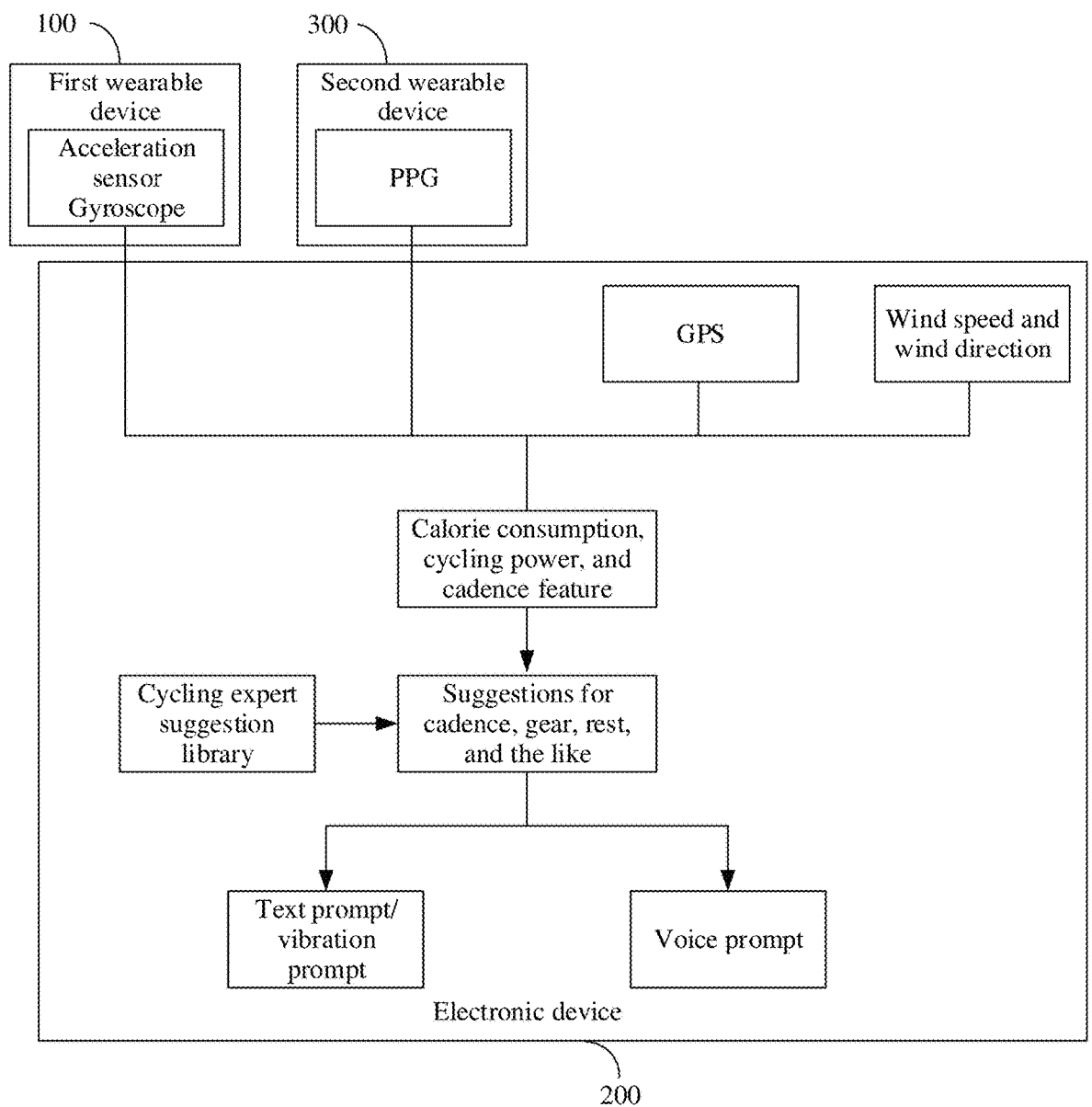
FIG. 11 is a schematic diagram of a method for generating a cycling suggestion according to an embodiment of this application.

As shown in FIG. 11, in still another application scenario, the electronic device 200 calculates a cadence feature and a foot posture feature based on the acceleration signal and the angular velocity signal collected by the first wearable device, and calculates calorie consumption of the user's cycling based on the heart rate information collected by the second wearable device, calculates a speed and a trajectory of the user's cycling based on the obtained location information, calculates a cycling power of the user's cycling based on the wind speed, the wind direction, and the speed, then calculates, based on the cycling power and the cycling time, a power of work done by the user during cycling, and then calculates cycling efficiency, namely, energy conversion efficiency based on the calorie consumption of the user's cycling and the work done by the user during cycling. The electronic device 200 compares the cadence feature, the foot posture feature, the speed, the calorie consumption, the cycling power, and the cycling efficiency of the user's cycling with preset cycling data to generate a cycling guidance suggestion. For example, the cycling guidance suggestion may be: adjusting a gear, adjusting a cadence, adjusting a seat, resting, or the like, to provide the user with professional cycling guidance. In a possible implementation, the electronic device 200 generates prompt information based on the cycling guidance suggestion, then generates a corresponding text prompt based on the prompt information, and displays it in the display interface, or sends the text prompt to the second wearable device 300, so that the second wearable device 300 displays it in a display interface. The electronic device 200 may alternatively generate a corresponding vibration prompt based on the prompt information, and indicate the electronic device 200 or the second wearable device 300 to vibrate based on the vibration prompt. The electronic device 200 may alternatively generate a corresponding voice prompt based on the prompt information, and send the voice prompt to an audio play device 400. The audio play device 400 is configured to play a corresponding voice based on the voice prompt. The user may adjust the cycling status based on the text prompt, the vibration prompts, or the voice prompt, thereby improving cycling experience of the user.

Figure 12:
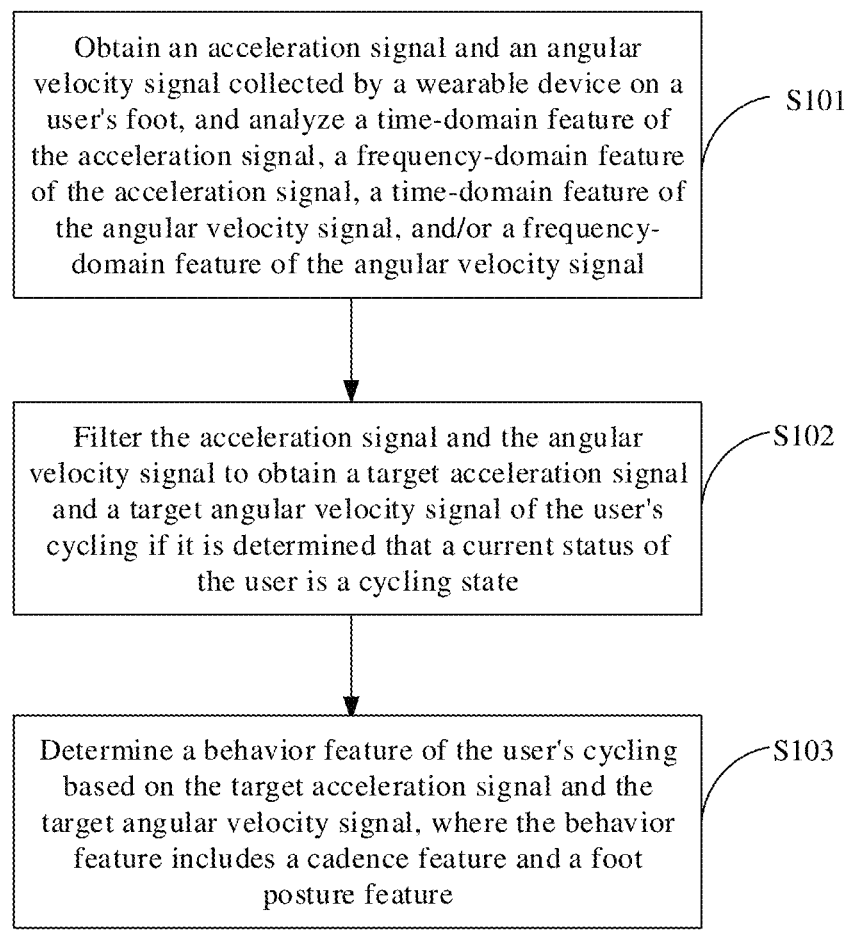
FIG. 12 is a schematic flowchart of a cycling detection method according to an embodiment of this application.

The following describes a cycling detection method provided in an embodiment of this application by using an example in which the method provided in this embodiment of this application is all performed by an electronic device. As shown in FIG. 12, the cycling detection method provided in this embodiment of this application includes the following steps.

S101: Obtain an acceleration signal and an angular velocity signal collected by a wearable device on a user's foot, and analyze a time-domain feature of the acceleration signal, a frequency-domain feature of the acceleration signal, a time-domain feature of the angular velocity signal, and/or a frequency-domain feature of the angular velocity signal.

The time-domain feature of the angular velocity signal includes an amplitude of a time-domain signal of an angular velocity in an α direction, an amplitude of the time-domain signal of the angular velocity in a β direction, and an amplitude of the time-domain signal of the angular velocity in a γ direction. The frequency-domain feature of the angular velocity signal is an amplitude of a frequency-domain signal of the angular velocity. The time-domain feature of the acceleration signal includes an amplitude of the time-domain signal of the acceleration in the α direction, an amplitude of the time-domain signal of the acceleration in the β direction, and an amplitude of the time-domain signal of the acceleration in the γ direction. The frequency-domain feature of the acceleration signal is an amplitude of the frequency-domain signal of the acceleration.

S102: Filter the acceleration signal and the angular velocity signal to obtain a target acceleration signal and a target angular velocity signal of the user's cycling if it is determined, based on an analysis result of the time-domain feature of the acceleration signal, the frequency-domain feature of the acceleration signal, the time-domain feature of the angular velocity signal, and/or the frequency-domain feature of the angular velocity signal, that a current status of the user is a cycling state.

In a possible implementation, if the amplitudes of the time-domain signal of the angular velocity in the three directions, the amplitude of the frequency-domain signal of the angular velocity, the amplitudes of the time-domain signal of the acceleration in the three directions, and the amplitude of the frequency-domain signal of the acceleration are all within preset amplitude ranges, the current status of the user is determined as the cycling state.

In another possible implementation, if any one of the amplitudes of the time-domain signal of the angular velocity in the three directions, the amplitude of the frequency-domain signal of the angular velocity, the amplitudes of the time-domain signal of the angular velocity in the three directions, and the amplitude of the frequency-domain signal of the angular velocity is within the preset amplitude range, the current status of the user is determined as the cycling state.

After determining that the current status of the user is the cycling state, the electronic device filters the acceleration signal and the angular velocity signal based on a preset frequency to obtain a filtered frequency-domain signal of the acceleration a filtered frequency-domain signal of the angular velocity. In the filtered frequency-domain signal of the angular velocity, if an amplitude within a preset frequency range meets a preset condition, an angular velocity frequency corresponding to the cycling state is determined based on a frequency corresponding to a largest amplitude within the preset frequency range. Similarly, an acceleration frequency corresponding to the cycling state is determined. After the angular velocity frequency corresponding to the cycling state and the acceleration frequency corresponding to the cycling state are determined, the angular velocity signal is filtered based on the angular velocity frequency corresponding to the cycling state to obtain a target angular velocity signal of the user's cycling, and the acceleration signal is filtered based on the acceleration frequency corresponding to the cycling state to obtain a target acceleration signal of the user's cycling.

S103: Determine a behavior feature of the user's cycling based on the target acceleration signal and the target angular velocity signal, where the behavior feature includes a cadence feature and a foot posture feature.

Specifically, a period of the target angular velocity signal is a period of pedaling during the user's cycling. A frequency at which the user pedals during cycling, namely, a cadence, may be calculated based on the period of pedaling. A target angular velocity signal in each half period is integrated to obtain a change of the angular velocity in the half period. The change of the angular velocity in the half period is a foot motion angle during the user's cycling, which is also the foot posture feature of the user's cycling, to guide the user's cycling.

In a possible implementation, the electronic device determines a pedal position at each moment of the user's cycling based on the target angular velocity signal, and then determines a foot position at each moment of the user's cycling based on the foot motion angle, and may determine a foot placement status of the user based on the pedal position and the foot position, and compare the foot placement state at each moment of the user's cycling with a preset placement status. If the foot placement status at each moment matches the preset placement status, it indicates that a seat height during the user's cycling is appropriate; otherwise, it indicates that the seat height during the user's cycling is not appropriate.

In a possible implementation, the electronic device obtains, from the target angular velocity signal, a time period in which the angular velocity value is 0 and marks this time period as a gliding time period of the user's cycling.

In a possible implementation, a first road surface feature may include a cement road surface, an asphalt road surface, a gravel road surface, tactile paving, and the like. Each road surface corresponds to a frequency range. The electronic device detects whether there is a band with an amplitude greater than a preset value in each frequency range of the frequency-domain signal of the angular velocity. If there is a band with an amplitude greater than the preset value, it indicates that the first road surface feature includes a road surface corresponding to the frequency range.

In a possible implementation, the electronic device obtains an acceleration signal collected by the wearable device on the user's foot when the user is standing or walking, where the acceleration signal collected when the user is standing or walking is an acceleration signal in a direction of gravity; and removes the acceleration signal in the direction of gravity from a target acceleration signal of at least one period to obtain a first acceleration signal. After obtaining the first acceleration signal, the electronic device uses a preset principal component analysis method to perform principal component analysis on the first acceleration signal, to obtain a first acceleration vector. A direction of the first acceleration vector is the same as a forward direction of the user's cycling, that is, parallel to a road surface. The electronic device can then determine a gradient of the road surface, namely, a second road surface feature, based on the direction of the first acceleration vector and a direction of a gravity vector.

After the direction of the gravity vector is determined, principal component analysis is performed on a target angular velocity signal of at least one period to obtain a lateral cycling vector. A direction of the lateral cycling vector is a direction of the angular velocity, and the direction of the angular velocity is perpendicular to a plane on which a bicycle is located. An opposite direction of the gravity vector is used as a Y-axis, the direction of the angular velocity is used as a Z-axis, an X-axis is determined based on the Y-axis and Z-axis, and in this case, the X-axis is along a horizontal direction, to construct a three-dimensional coordinate system. After the three-dimensional coordinate system is constructed, coordinates in the three-dimensional coordinate system during the user's cycling are calculated based on a value and a direction of the first acceleration vector. A moving trajectory in the three-dimensional coordinate system during the user's cycling, namely, a cycling trajectory of the user on a slope road surface, may be obtained based on coordinates in the three-dimensional coordinate system at each moment of the user's cycling. The cycling trajectory includes both a forward trajectory on the road surface during the user's cycling and a left-right moving trajectory on the road surface during the user's cycling.

In a possible implementation, the electronic device further obtains location information of the user during cycling, and can calculate a cycling speed of the user based on the location information. The location information may be collected by the electronic device, or may be obtained by the electronic device from a second wearable device that is worn by the user. After calculating the cycling speed of the user, the electronic device calculates a cycling power of the user based on the speed and resistance needing to be overcome during the user's cycling. The resistance needing to be overcome during the user's cycling includes wind resistance, friction force, and gravity. The electronic device may determine the wind resistance based on an obtained wind speed and wind direction, may determine the friction force based on obtained preset friction force experience values, and may determine the gravity based on the user's weight. After calculating the cycling power of the user, the electronic device may determine, based on the cycling power and a cycling time, energy consumed by the user's cycling.

In a possible implementation, the electronic device further obtains heart rate information of the user during cycling from the second wearable device, and determines energy consumed by the user during cycling based on the heart rate information of the user during cycling and a preset calculation formula. Cycling efficiency of the user's cycling may be calculated based on work done by the user during cycling and the energy consumed by the user during cycling.

In a possible implementation, the electronic device further obtains preset cycling data, generates a cycling guidance suggestion based on the preset cycling data, the cycling efficiency, the cycling power, the cadence feature, and the foot posture feature, and generates at least one of a corresponding text prompt, voice prompt, or vibration prompt based on the cycling guidance suggestion, to provide professional guidance for the user's cycling and improve user experience.

In the foregoing embodiment, the acceleration signal and the angular velocity signal collected by the wearable device of the foot are obtained. First, a status of the user is identified based on the time-domain feature of the acceleration signal, the frequency-domain feature of the acceleration signal, the time-domain feature of the angular velocity signal, and the frequency-domain feature of the angular velocity signal. Then, the angular velocity signal and the angular velocity signal are filtered to obtain the target acceleration signal and the target angular velocity signal of the user's cycling if the status of the user is the cycling state. An interference signal may be removed by determining the cycling state and performing filtering, to obtain accurate cycling data of the user, thereby improving calculating precision. Finally, a behavior feature of the user's cycling is determined based on a waveform feature of the target acceleration signal and a waveform feature of the target angular velocity signal of the user's cycling. The behavior feature of the user's cycling is determined based on the acceleration signal and the angular velocity signal of the user's foot collected during cycling. Therefore, when compared with determining the behavior feature of the user's cycling based on motion information of a bicycle, more behavior features of the user's cycling may be determined, including the cadence feature and the foot posture feature of the user's cycling, to improve accuracy of a cycling behavior analysis result and better guide the user's cycling. In addition, the wearable device on the foot is easy to use, thereby improving user experience with ease of use and practicability.

It should be understood that a sequence number of the step in the foregoing embodiment does not mean an order of execution, and an order of execution of each process should be determined by a function of the process and internal logic, and shall not constitute any limitation on an implementation process of the embodiment of this application.

Figure 13:
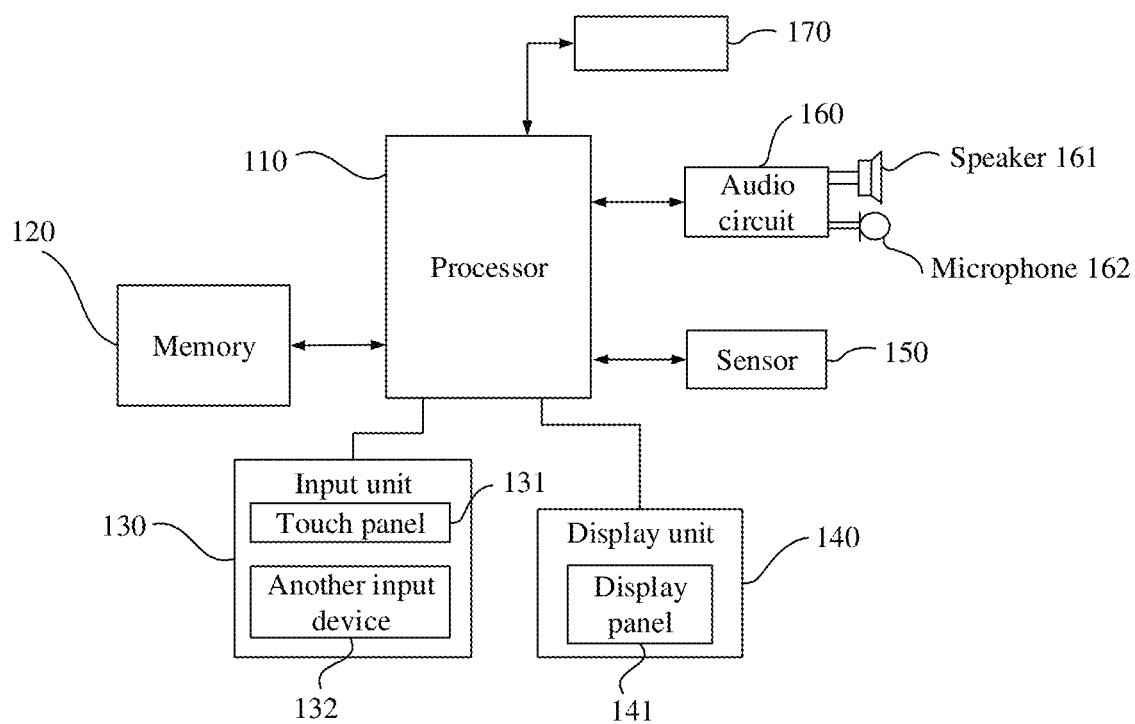
FIG. 13 is a schematic diagram of an electronic device according to an embodiment of this application.

Based on a same invention conception, an embodiment of this application further provides an electronic device. As shown in FIG. 13, the electronic device provided in this embodiment of this application includes a processor 110, a memory 120, an input unit 130, a display unit 140, a sensor 150, an audio circuit 160, and a communication module 170. A person skilled in the art may understand that a structure shown in FIG. 13 does not constitute any limitation on the electronic device, and may include more or fewer components than those shown in the figure, or combine some components, or have a different component arrangement.

The memory 120 may be configured to store a software program and a module. The processor 110 performs various functional applications of the electronic device and processes data by running the software program and the module stored in the memory 120. The memory 120 may mainly include a program storage area and a data storage area. The program storage area may store an operating system, an application required for at least one function (such as a sound play function and an image play function), and the like. The data storage area may store data created based on use of the electronic device (such as audio data and a phone book), and the like. In addition, the memory 120 may include a high-speed random access memory, and may further include a non-volatile memory, for example, at least one magnetic disk storage device, a flash memory device, or another volatile solid-state storage device.

The input unit 130 may be configured to receive input digit or character information and generate key signal input related to user settings and function control of the electronic device. Specifically, the input unit 130 may include a touch panel 131 and another input device 132. The touch panel 131, also referred to as a touchscreen, may collect a touch operation performed by a user on or near the touch panel 131 (for example, an operation performed by the user on the touch panel 131 or near the touch panel 131 by using any appropriate object or accessory such as a finger or a stylus) and drive a corresponding connection apparatus based on a preset program. Optionally, the touch panel 131 may include two parts: a touch detection apparatus and a touch controller. The touch detection apparatus detects a touch direction and position of the user, detects a signal generated by a touch operation, and transmits the signal to the touch controller. The touch controller receives touch information from the touch detection apparatus, converts the touch information into point coordinates, and sends the point coordinates to the processor 110; and can receive and execute a command sent by the processor 110. In addition, the touch panel 131 may be implemented as a resistive type, a capacitive type, an infrared type, a surface acoustic wave type, or the like. The input unit 130 may further include the another input device 132 in addition to the touch panel 131. Specifically, the another input device 132 may include but is not limited to one or more of a physical keyboard, a function button (such as a volume control button or an on/off button), a trackball, a mouse, a joystick, and the like.

The display unit 140 may be configured to display information entered by the user, information provided for the user, and various menus of the electronic device. The display unit 140 may include a display panel 141. Optionally, the display panel 141 may be configured in a form of a liquid crystal display (Liquid Crystal Display, LCD), an organic light-emitting diode (Organic Light-Emitting Diode, OLED), or the like. Further, the touch panel 131 can cover display panel 141. When detecting a touch operation on or near the touch panel 131, the touch panel 131 transmits the touch operation to the processor 110 to determine a type of a touch event. Then, the processor 110 provides corresponding visual output on the display panel 141 based on the type of the touch event. Although the touch panel 131 and the display panel 141 are used as two separate components to implement input and input functions of the electronic device in FIG. 13, in some embodiments, the touch panel 131 and the display panel 141 may be integrated to implement the input and output functions of the electronic device.

The electronic device may further include at least one type of sensor 150, such as a light sensor, a motion sensor, and another sensor. Specifically, the light sensor may include an ambient light sensor and a proximity sensor. The ambient light sensor may adjust brightness of a display panel 141 based on intensity of ambient light. The proximity sensor may turn off the display panel 141 and/or backlight when the electronic device moves close to an ear. As a type of motion sensor, an accelerometer sensor may detect values of acceleration in various directions (there are usually three axes), may detect a value and a direction of gravity when the electronic device is still, and may be used for an application of recognizing a posture of the electronic device (for example, landscape/portrait mode switching, a related game, or magnetometer posture calibration), a vibration recognition related function (for example, a pedometer or a keystroke), and the like. For other sensors that can be configured for the electronic device, such as a gyroscope, a barometer, a hygrometer, a thermometer, or an infrared sensor, details are not described further herein.

The audio circuit 160, a speaker 161, and a microphone 162 may provide an audio interface between a user and the electronic device. The audio circuit 160 can transmit, to the speaker 161, an electrical signal converted from received audio data, and the speaker 161 converts the electrical signal into a sound signal for outputting. In addition, the microphone 162 converts a collected sound signal into an electrical signal, and audio circuit 160 receives it and then converts it into audio data. Then the audio data is output to the processor 110 for processing, and then sent to, for example, another electronic device through the RF circuit 110, or the audio data is output to the memory 120 for further processing.

The communication module 170 may be configured to support data exchange of wireless communication, including BT, WLAN (such as Wi-Fi), Zigbee, FM, NFC, IR, universal 2.4G/5G, or other wireless communication technologies, between the electronic device and another electronic device.

The processor 110 is a control center of the electronic device, connects to various parts of the entire electronic device by using various interfaces and lines, and executes various functions and data processing of the electronic device by running or executing a software program and/or a module stored in the memory 120 and invoking data stored in the memory 120, so as to perform overall monitoring on the electronic device. Optionally, the processor 110 may include one or more processing units. Preferably, the processor 110 may integrate an application processor and a modem processor. The application processor mainly processes an operating system, a user interface, an application program, and the like. The modem processor mainly processes wireless communications. It can be understood that the foregoing modem processor may not be integrated into the processor 110.

It should be noted that content such as information exchange between and execution processes of the foregoing apparatus/units is based on a same concept as the method embodiment of this application. Therefore, for specific functions and technical effects thereof, refer to the method embodiments. Details are not described herein again.

In the foregoing embodiments, the descriptions of various embodiments have respective focuses. For a part that is not described or recorded in detail in an embodiment, reference may be made to related descriptions in other embodiments.

A person skilled in the art may clearly understand that for the purpose of convenient and brief descriptions, division into the foregoing functional unit or modules is merely used as an example for description. During actual application, the foregoing functions may be allocated to different functional unit or modules for implementation according to a requirement, that is, an internal structure of the apparatus is divided into different functional units or modules to implement all or some of the functions described above. Functional units or modules in the embodiments may be integrated into one processing unit, or each of the units may exist alone physically, or two or more units may be integrated into one unit. The integrated unit may be implemented in a form of hardware, or may be implemented in a form of a software function unit. In addition, specific names of the functional units or modules are merely for convenience of distinguishing from each other, and are not intended to limit the protection scope of this application. For specific working processes of units or modules in a system described above, refer to corresponding processes in the foregoing method embodiments. Details are not described herein again.

When the integrated unit is implemented in the form of a software function unit and is sold or used as an independent product, the integrated unit may be stored in a computer-readable storage medium. Based on such an understanding, all or a part of the procedure of the method in the foregoing embodiments of this application may be implemented by a computer program instructing relevant hardware. The computer program may be stored in a computer-readable storage medium. When the computer program is executed by a processor, the steps of the method embodiments may be implemented. The computer program includes computer program code, and the computer program code may be in the form of source code, object code, or an executable file, or in some intermediate forms, or the like. The computer-readable medium may include at least any entity or apparatus capable of carrying the computer program code to a photographing apparatus/electronic device, a recording medium, a computer memory, a read-only memory (ROM, Read-Only Memory), a random access memory (RAM, Random Access Memory), an electrical carrier signal, a telecommunication signal, or a software distribution medium, such as a USB flash drive, a mobile hard disk, a magnetic disk, or an optical disc.

The units described as separate parts may or may not be physically separate, and parts displayed as units may or may not be physical units, may be located in one position, or may be distributed on a plurality of network units. Some or all of the units may be selected according to an actual requirement to achieve the objectives of the solutions of the embodiments.

In the embodiments provided in this application, it should be understood that the disclosed apparatus/network device and method may be implemented in other manners. For example, the described apparatus/network device embodiment is merely an example. For example, the module or unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

A person of ordinary skill in the art may be aware that units and algorithm steps in the examples described with reference to the embodiments disclosed in this specification may be implemented by electronic hardware or a combination of computer software and electronic hardware. Whether the functions are performed by hardware or software depends on particular applications and design constraint conditions of the technical solutions. A person skilled in the art may use different methods to implement the described functions for each particular application, but it should not be considered that the implementation goes beyond the scope of this application.

Finally, it should be noted that the foregoing descriptions are merely specific implementations of this application, but the protection scope of this application is not limited thereto. Any variation or replacement within the technical scope disclosed in this application shall fall within the protection scope of this application. Therefore, the protection scope of this application shall be subject to the protection scope of the claims.

The invention claimed is:

1. A cycling detection method, comprising:
obtaining an acceleration signal and an angular velocity signal collected by a wearable device on a user's foot, and analyzing a time-domain feature of the acceleration signal, a frequency-domain feature of the acceleration signal, a time-domain feature of the angular velocity signal, and/or a frequency-domain feature of the angular velocity signal;
filtering the acceleration signal and the angular velocity signal to obtain a target acceleration signal and a target angular velocity signal of the user's cycling if it is determined, based on an analysis result of the time-domain feature of the acceleration signal, the frequency-domain feature of the acceleration signal, the time-domain feature of the angular velocity signal, and/or the frequency-domain feature of the angular velocity signal, that a current status of the user is a cycling state; and
determining a behavior feature of the user's cycling based on the target acceleration signal and the target angular velocity signal, wherein the behavior feature comprises a cadence feature and a foot posture feature.

2. The method according to claim 1, wherein after the obtaining an acceleration signal and an angular velocity signal collected by a wearable device on a foot of a user, the method further comprises:
determining a first road surface feature of the user's cycling based on the frequency-domain feature of the angular velocity signal.

3. The method according to claim 1, after the obtaining a target acceleration signal and a target angular velocity signal of the user's cycling, the method further comprises:
determining a second road surface feature of the user's cycling based on the target acceleration signal.

4. The method according to claim 3, wherein the determining a second road surface feature based on the target acceleration signal comprises:
obtaining a prestored acceleration signal collected when the user is standing or walking;
determining a direction of a gravity vector based on the acceleration signal collected when the user is standing or walking;
determine a direction of a first acceleration vector of the user's cycling based on the acceleration signal collected when the user is standing or walking and the target acceleration signal; and
determining the second road surface feature based on the direction of the first acceleration vector and the direction of the gravity vector.

5. The method according to claim 4, wherein after the determining the second road surface feature based on the direction of the first acceleration vector and the direction of the gravity vector, the method further comprises:
constructing a three-dimensional coordinate system, wherein an X-axis in the three-dimensional coordinate system represents a horizontal direction of cycling, a Y-axis represents an opposite direction of the gravity vector, a Z-axis represents a direction of an angular velocity, and the direction of angular velocity is determined by the target angular velocity signal; and
determining, based on the first acceleration vector and the three-dimensional coordinate system, a cycling trajectory corresponding to the second road surface feature.

6. The method according to claim 1, wherein the method further comprises:
obtaining resistance and a cycling speed of the user's cycling; and
calculating a cycling power of the user based on the resistance and the cycling speed.

7. The method according to claim 6, wherein the obtaining resistance of the user's cycling comprises:
   obtaining a wind speed, a wind direction, and a weight of the user; and
   determining the resistance of the user's cycling based on the wind speed, the wind direction, and the weight of the user.

8. The method according to claim 7, wherein the method further comprises:
   obtaining heart rate information of the user during cycling; and
   determining energy consumed by the user during cycling based on the heart rate information of the user during cycling and a preset calculation formula.

9. The method according to claim 8, wherein the method further comprises:
   calculating, based on the cycling power, work done by the user during cycling; and
   calculating cycling efficiency of the user's cycling based on the work done by the user during cycling and the energy consumed by the user during cycling.

10. The method according to claim 9, wherein the method further comprises:
    obtaining preset cycling data; and
    generating a cycling guidance suggestion based on the preset cycling data, the cycling efficiency, the cycling power, the cadence feature, and the foot posture feature.

11. The method according to claim 10, wherein the method further comprises:
    generating at least one of a corresponding text prompt, voice prompt, or vibration prompt based on the cycling guidance suggestion.

12. An electronic device, comprising a memory, a processor, and a computer program stored in the memory and executable on the processor, wherein when the processor implements the computer program, the method according to claim 1 is implemented.

13. A non-transitory computer-readable storage medium, wherein the non-transitory computer-readable storage medium stores a computer program, and when the computer program is executed by a processor, the method according to claim 1 is implemented.

* * * * *